US006190886B1

(12) United States Patent
Hoppe et al.

(10) Patent No.: US 6,190,886 B1
(45) Date of Patent: Feb. 20, 2001

(54) TRIMERIZING POLYPEPTIDES, THEIR MANUFACTURE AND USE

(76) Inventors: Hans-Jürgen Hoppe; Kenneth B. Reid, both of MRC Immunochemistry Unit, Dept. of Biochemistry, University of Oxford, South Parks Road, OX1 3QU, Oxford (GB)

(*) Notice: Under 35 U.S.C. 154(b), the term of this patent shall be extended for 0 days.

(21) Appl. No.: 08/737,629

(22) PCT Filed: May 16, 1995

(86) PCT No.: PCT/GB95/00104

§ 371 Date: Jan. 10, 1997

§ 102(e) Date: Jan. 10, 1997

(87) PCT Pub. No.: WO95/31540

PCT Pub. Date: Nov. 23, 1995

(30) Foreign Application Priority Data

May 16, 1994 (GB) .................................................. 9409768

(51) Int. Cl.[7] .......................... C12N 15/00; C07K 14/46; C07K 19/00; C07H 21/04
(52) U.S. Cl. ..................... 435/69.7; 435/325; 435/252.3; 435/320.1; 530/324; 530/356; 530/387.3; 530/402; 536/23.4
(58) Field of Search ..................................... 530/324, 356, 530/387.3, 402; 536/23.4; 435/69.7, 325, 252.3, 320.1

(56) References Cited

U.S. PATENT DOCUMENTS 5,716,805 * 2/1998 Srinivasan et al. .................. 435/69.1

OTHER PUBLICATIONS

Bowie et al. Deciphering the message in protein sequences: tolerance to amino acid substitutions. Science, (Mar. 16, 1990) 247 (4948) 1306–10.*
Labourdette et al. Analysis of the role of the COL1 domain and its adjacent cysteine–containing sequence in the chain assembly of type IX collagen. FEBS Letters, (Apr. 12 1993) 320 (3) 211–4.*
Flick et al. Yeast heat shock transcription factor contains a flexible linker between the DNA–binding and trimerization domains. Implications for DNA binding by trimeric proteins. J.Biol. Chem., (Apr. 29, 1994) 269 (17) 12475–81.*

FEBS LETTERS., vol. 344, No. 2–3, May 16, 1994, Amsterdam NL pages 191–195, H–J Hoppe et al. A parallel three stranded alpha–helical bundle at the nucleation site of collagen triple–helix formation.
Journal of Biological Chemistry, vol. 269, No. 16, Apr. 22, 1994, Baltimore, MD U.S., pp. 11820–11824, B–L LIM et al. "Primary structure of bovine collectin–43 (CL–43)".
Molecular Immunology vol. 30, No. SUP1, 1993 page 18, H–J Hoppe & K B M Reid "studies on the domain structure of recombinant HSP–D provide a model for trimerisatin of collectins and C1Q".
Immunology Today, vol. 15, No. 2, Feb. 1994, Cambridge GB pp. 67–64, U Holmskov et al. "Collectins; collagenous c–type lectis of the innate immune defense sysetm".
Biochemical and Biophysical Research Communications., vol.202, No. 3, Aug. 15, 1994, Duluth, Minnesota U.S. pp. 1674–1680, B–L LIM et al., Expression of the carbohydrate recognition domain of lung surfactant protein D and demonstration of its binding to lipopolysaccharides of Gram–negative bacteria.
Armitage, Richard J. et al., "CD40 Ligand is a T Cell Growth Factor", Eur. J. Immunol., vol. 23, 1993, pp. 2326–2331.
Peteranderl, Ralph et al., "Trimerization of the Heat Shock Transcription Factor . . . ", Biochemistry, vol. 31, No. 48, 1992, pp. 12272–12276.
Sorger, Peter K. et al., "Trimerization of a Yeast Transcriptional Activator . . .", Cell, vol. 59, Dec. 1, 1989, pp. 807–812.

* cited by examiner

Primary Examiner—David Romeo
(74) Attorney, Agent, or Firm—Nixon & Vanderhye P.C.

(57) ABSTRACT

Polypeptides comprising a collectin neck region, or variant or derivative thereof or amino acid sequence having the same or a similar amino acid pattern and/or hydrophobicity profile, are able to trimerize. Such polypeptides may comprise additional amino acids which may include heterologous amino acids, for example, forming a protein domain or derived from an immunoglobulin or comprising an amino acid which may be derivatized for attachment of a non-peptide moiety such as oligosaccharide, and may form homotrimers or heterotrimers. Heterotrimerization may be promoted by gentle heating, e.g. to about 50° C., then cooling to room temperature. One use for the polypeptides is in seeding collagen formation. Nucleic acid encoding the polypeptides and methods of their production are provided.

63 Claims, 16 Drawing Sheets

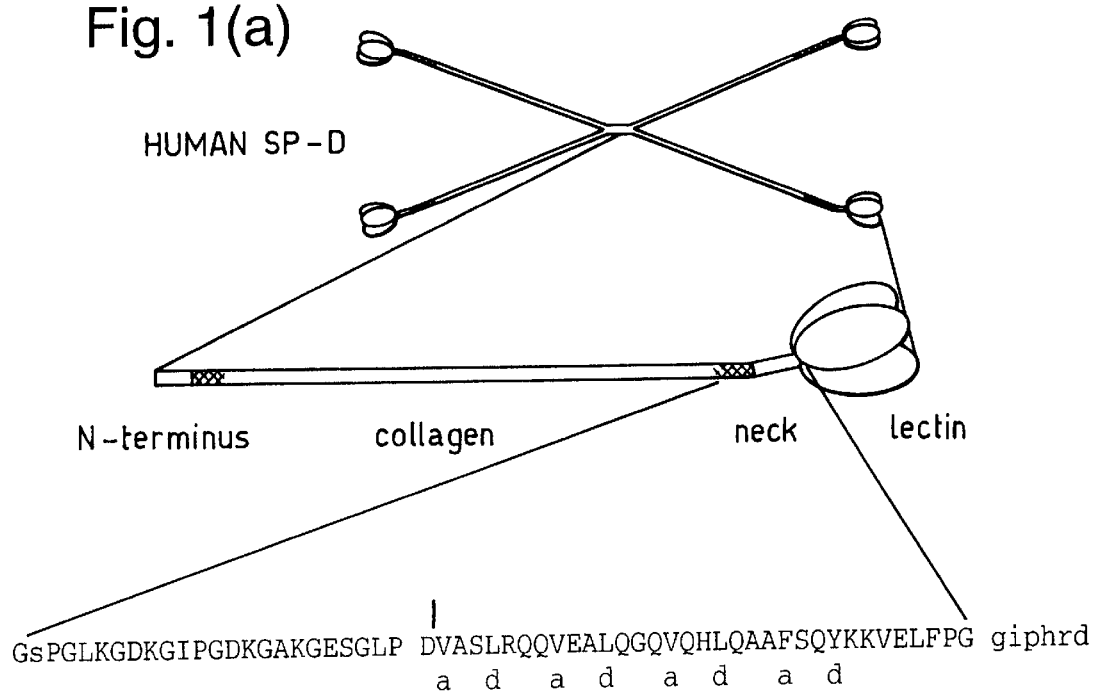

THROMBIN
↓

R-gs<u>AEMKTYSHRTPSACTLVMCSSESGLPGR</u>
GLKGDKGIPGDKGAKGESGLPDVASLRQQVEALQGQVQHLQAAFSQYKKVELFPNGgiphrd*

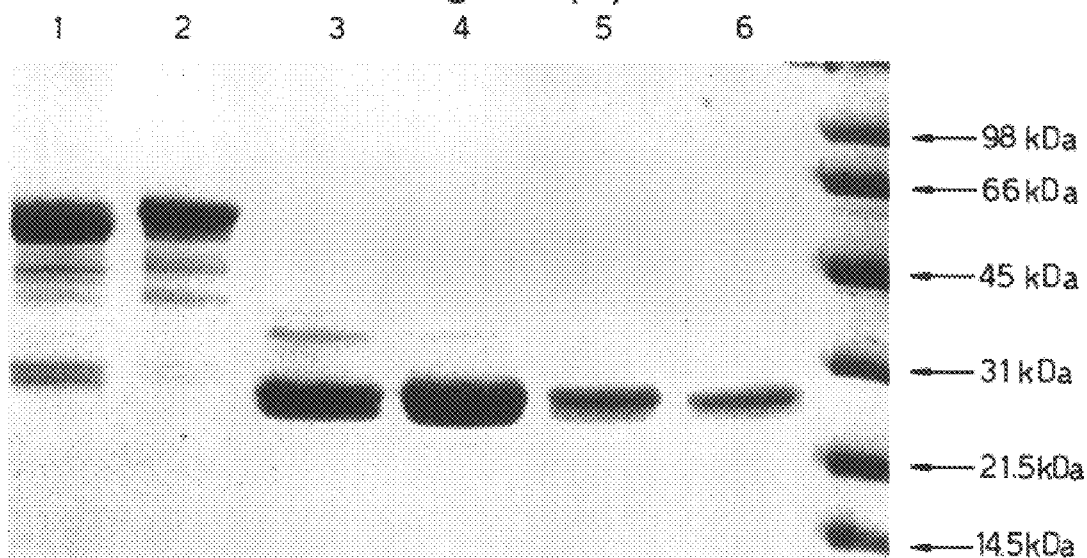

TRIMERIZING POLYPEPTIDES, THEIR MANUFACTURE AND USE

This Application is a 371 of PCT/GB95/0114, filed May 16, 1995.

The present invention relates to polypeptides able to form multimers, particularly trimers, and manufacture and use of such polypeptides.

The biosynthesis of collagen molecules requires the correct alignment of three polypeptides consisting of Gly-Xaa-Yaa triplets to form the triple-helix [1]. Each chain assumes a left-handed helical structure in the right-handed triple-helix, which is stabilized by inter-chain hydrogen bonds. The formation of the triple helix proceeds from a single nucleation point at the C-terminal end of the three chains and grows in a zipper-like fashion [2].

Refolding experiments on collagen type III indicated that specific inter-chain disulphide-bridges formed between C-terminal globular protein structures, can be sufficient to function as a nucleus for the refolding of a triple-helix in vitro, whereas reduction abrogates this process completely [3]. However, the molecular mechanism guiding association and registered alignment of collagens has remained elusive since the family of proteins containing collagenous sequences is large and sequence comparison of the different types of C-terminal, non-collagen-like, regions did not reveal a common motif shared by FACITs (fibril associated collagens with interrupted triple-helix, types IX, XII, XIV, and XVI), the collagens of striated fibrils (types I, II, III, V, and XI), or the collagens with Clq-like C-terminal domains (types VIII and X) [4]. The frequent formation of inter-chain disulphide bonds has further complicated the search for protein modules involved in the inter-chain association and subsequent nucleation of triple-helix formation.

The family of collagenous proteins known as the "collectins" is composed of the serum proteins mannan-binding protein (MBP), collectin-43 and bovine conglutinin as well as the lung surfactant proteins SP-D and SP-A [5]. Collectin polypeptide chains contain a short N-terminal region, a collagen-like region (of between 20 and 59 Gly-Xaa-Yaa triplets) linked, by a short stretch of 34–39 amino acids (which form the 'neck' region) to a C-terminal, C-type lectin domain (of 113–118 amino acids) (FIG. 1a).

The present invention has resulted from results showing that the "neck-region" of collectin protein is able to mediate inter-chain recognition, trimerization and registered alignment of three collagenous polypeptide chains [7]. The results make available simple means of trimerising polypeptides of choice.

According to the present invention there is provided a polypeptide comprising a neck-region of a collectin, or an amino acid sequence variant thereof or a derivative thereof. Such polypeptide will form a trimer under appropriate conditions. The polypeptide is non-naturally occurring, i.e. it is one not found in nature.

It may comprise one or more heterologous amino acids joined to the neck-region or variant or derivative thereof. It may retain one or more amino acids from the molecule from which is it derived; for example the polypeptide may comprise a collectin C-type lectin domain.

According to one definition, the present invention provides a non-naturally occurring polypeptide consisting essentially of amino acids according to the following formula:

wherein N is a collectin neck-region peptide or a variant or derivative thereof or a sequence of amino acids having an amino acid pattern and/or hydrophobicity profile which is the same as or similar to that of a collecting neck-region, able to form a trimer; X is absent or one or more amino acids and Y is absent or one or more amino acids. If X and Y are both absent, the polypeptide consists essentially of N. X and/or Y may comprise one or more heterologous amino acids, any of which may be derivatisable, or "chemically modifiable", for attachment of a chemical moiety.

The chemical moiety may be introduced at a specific chemically modifiable residue or residues. A chemically modifiable amino acid residue is an amino acid residue susceptible to modification with a chosen chemical reagent under specified conditions. The amino acid may be unique in the polypeptide or it may be uniquely modifiable, or selectively or preferentially modifiable over other amino acids present. For instance, a cysteine residue may be introduced into the binding site and be available for chemical modification via its thiol group. It may also be possible to render an amino acid preferentially modifiable compared with other amino acids of the same type within the molecule by engineering its environment, eg by positioning it within the molecule adjacent another amino acid with particular properties. For instance, an amino group next to a carboxlate group would be rendered more nucleophilic and selectively modifiable even if not unique within the binding site.

Other chemically modifiable amino acids include lysine, glutamate, histidine and tyrosine.

Covalent modification allows a wide variety of moieties to be incorporated, particularly reporter groups or cofactors for catalysis. In one embodiment of the present invention, one or more amino acids which are specifically modifiable are incorporated. This allows the interaction of large organic groups such as the fluorescent reporter group, 7-nitrobenz-2-oxa-1,3-diazole (NBD). Other large groups such as the flavin cofactors for catalysis, FMN and FAD may be incorporated.

There is also the possibility of incorporating two (or more) residues for modification with the same reagent or two (or more) different reagents, or more preferably different residues may be modified with different reagents to incorporate different chemical moieties into the binding site. This is useful eg for catalysis where the presence of two chemical moieties such as flavin and haem may promote catalysis of a redox reaction.

There are other possible ways of modifying a polypeptide. There are a number of amino acid residues which may be specifically derivatized using molecules containing specific functional groups. For instance, amino groups may be modified with N-hydroxysuccinimide esters, carboxyl groups with carbodiimides, histidines and cysteines with halomethyl ketones, arginine with glyoxals (see e.g. A. R. Fersht, Enzyme Structure and Mechanism 2nd edn, 1985 pp248–251, W. H. Freeman, New York).

Some reagents which may be used to modify specific amino-acid residues are given by T. Imoto and H. Yamada in "Protein Function: a Practical Approach", pp247–277, 1989. To introduce specific functional groups into polypeptides the reactive group of these reagents may be combined with the functional group in a modifying reagent. For instance, if it is desired to modify a protein with the fluorophore 7-amino-4-methylcoumarin-3-acetic acid, the N-hydroxysuccinimidyl ester of the molecule may be used to modify amino groups, whereas N-[6-(-amino-4-methylcoumarin-3-acetamido)hexyl]-3'-(2'-pyridyldithio) propionamide may be used to modify cysteine groups.

Another possible methodology is to use transglutaminase which catalyzes an acyl-transfer reaction between the gamma-carboxyamide group of glutamine residues and primary amines (E. Bendixen et al, J. Biol. Chem. 26821962–21967, 1993; K. N. Lee et al Biochim. Biophys. Acta 1202 1–6 1993; T. Kanaji et al J. Biol. Chem. 268 11565–11572 1993). This enzyme could therefore introduce amino acid residues from a peptide into a glutamine residue through a peptide lysine epsilon amino group or into a lysine group via a peptide glutamine group. The enzyme could also catalyse derivatization of glutamine residues with a primary amine.

A further approach is to introduce chemical moieties to either the N or C terminus of a polypeptide using reverse proteolysis or chemical conjugation or a combination of the two (I. Fisch et al, Bioconj. Chem. 3, 147–153, 1992; H. F. Gaertner et al, Bioconjug. Chem. 3, 262–268, 1992; H. F. Gaertner et al, J. Biol. Chem. 269, 7224–7230, 1994; J. Bongers et al, Biochim. Biophys. Acta, 50, S57–162, 1991; R. Offord, Protein Engineering, 4, 709–710, 1991). These methods have been used to introduce non-encoded elements to protein and peptide molecules.

Examples of fluorophores which may be introduced are fluorescein, phycoerythrin, coumarin, NBD, Texas Red and chelated lanthanide ions. Examples of catalytic groups which may be introduced are flavin adenine dinucleotide (FAD), flavin mononucleotide (FMN), cytochromes and chelated metal ions such as zinc and copper.

In one embodiment the neck-region is that of the collectin SP-D (or a variant or derivative thereof). Other possibilities include collectin-43 and conglutinin. Mannan-binding protein (MBP) and SP-A may also be useable in the present invention, though in that case additional amino acids from the respective lectin domains may be required. Since, however, those additional amino acids may have α-helical structure, as in the natural molecule, the sequence of amino acids required may still be considered to be the "neck region" of the collectin.

FIG. 1(a) shows the neck-region of SP-D, with V/L repeat. In certain embodiments it is preferred to include in the neck-region the immediately up stream G residue, and amino acids in between, and/or downstream linker, such as the one shown. A linker may be important for spacing folded domains in a trimer. For instance, " . . . FP . . . " may provide a kink in the chain.

If not the neck-region of SP-D, the neck-region in a polypeptide according to the present invention may have an amino acid pattern and/or hydrophobicity profile the same as or similar (e.g. substantially the same as) to that of the neck-region of SP-D, provided the ability to trimerise is retained.

The following shows an alignment of amino acids in various collectin neck regions:
position—abcdefgabcdefgabcdefgabcdef
human     SP-D—VASLRQQVEALQGQVQHLQAAFSQYKK (SEQ ID NO:1)
bovine          SP-D—VNALRQRVGILEGQLQRLQNAFSQYKK (SEQ ID NO:2)
rat    SP-D—SAALRQQMEALNGKLQRLEAAFSRYKK (SEQ ID NO:3)
bovine   conglutinin   VNALKQRVTILDGHLRRFQNAFSQYKK (SEQ ID NO:4)
bovine   collectin   43   VDTLRQRMRNLEGEVQRLQNIVTQYRK (SEQ ID NO:5)

The positioning of V at layer 'a' and L at layer 'd' was commonly believed to result preferably in dimers. The presence of F and Y in the above sequences is unusual and may have a direct influence on the degree of oligomerization. G is positioned exactly in the middle of the two 'ad' repeats. This may also be of importance for the trimerization process. Glycine residues behave slightly different than other residues in α-helices; however, no clear rules are established so far: G is often found at the end of helices, terminating them. Since residues of the 'a' and 'd' layers do not exactly come to be positioned on top of one another ('a1' on top of 'a2', 'd1' on top of 'd2') in the left-handed supercoil of the α-helical bundle, the central positioned glycine residue might be relevant for a slightly altered supercoil of the helices, and thus for a different packing behaviour or the hydrophobic residues at the 'a' and 'd' layers. This in turn may be part of the reason for the exclusive trimerization of the given sequence. The C-terminal 'ad' layers of rather large, bulky hydrophobic residues F and Y will require a different packing behaviour than the standard α-helical bundle, possibly also affecting the overall twist and geometry of the coiled-coil. The abundant presence of Q residues might also be important, since Q residues at 'e' and 'g' positions can contribue also to the forces holding the helices together, and this is emphasised by the substitutions seen from human SP-D to, for example, bovine collectin 43, where a Q to R substition at the 'g' position is paralleled by a Q to E substition at the 'e' layer of directly following 'a–g' repeat, thus providing for a ionic interaction with opposite charges at the positions of the Q residues in human SP-D.

The neck-region peptide has therefore a number of distinct features which may be altered perhaps to influence the properties of the peptide to form a trimeric α-helical bundle. The alignment shows naturally occurring neck-regions of collectins which form trimers and which also show a number of substitutions, apparently not affecting the trimerizing capability.

Trimerising features of the neck-region peptide may be further enhanced by lengthening of the "a"–"d" repeats, particularly at the N-terminal end, for instance by addition of another copy of the first part of the neck region:
VASLRQQVEALQGQ-VASLRQQVEALQ GQVQHLQAAFSQYKK (SEQ ID NO:6)

For human administration purposes, preferably the neck-region and/or the heterologous sequence of amino acids are human in origin, or "humanized", in order to reduce the likelihood of there being an immune response generated upon administration of the polypeptide to an individual. The term "heterologous sequence of amino acids" refers to a chain of amino acids which is not found naturally joined to the collectin neck-region at the position of fusion in the polypeptide of the invention.

Amino acids joined to the neck region (etc.) may form a protein domain. Preferably, the sequence of amino acids forms a functional domain. The amino acids may comprise a sequence derived from an immunoglobulin, eg variable domain, or variable domain and constant region.

In principle, any amino acid sequence including a peptide or polypeptide, independently folding protein domain or protein domains may be joined to the neck-region peptide. This may be at the C-terminal or the N-terminal end of the polypeptide or at both ends, involving identical, similar, or different protein sequences. "Joining" may involve use of recombinant DNA technology to generate a fusion polypeptide or the use of chemical synthesis of a polypeptide including the neck-region (or a variant thereof or derivative thereof) or the chemical attachment of polypeptides to the neck-region peptide.

Any three identical or different polypeptides containing the neck-region may form homo-trimers or hetero-trimers under appropriate conditions. A homotrimer consists of three polypeptides which are the same. A heterotrimer consists of three polypeptides, at least two of which are different. All three polypeptides may be different. One, two or all three polypeptides in a heterotrimer may be a polypeptide according to the invention, provided each polypeptide has a region able to trimerise.

The neck-region α-helical bundle generally exists only as a trimeric molecule in conditions which mimic or approximate physiological conditions. The stability of the trimer may be enhanced by increasing the ionic strength of the solution. The trimeric association may be reversibly broken up by denaturation (e.g. heat denaturation) and the molecules can re-associate into trimers as soon as conditions return to physiological conditions (cooling). The neck-region peptide's ability to trimerize is independent of adjacent protein sequences. Using different polypeptides, each containing the neck-region, the reversible denaturation-reassociation process can be used to form heterotrimeric molecules. Preferably, the conditions for denaturation are chosen to prevent loss of any property of the adjacent heterologous protein domain. One method of producing heterotrimers is specified in Example 3 and involves heating (in this case to about 50° C.) and cooling.

The heterotrimerization using about 50° C. is only an example at a certain ionic strength; other means of heterotrimerizations may be preferable. The methods employed may vary depending on the application. The different neck-region peptide constructs can be chemically synthesized, modified, or generated in an expression system. A chemical attachment site can be as specific as a fusion-protein, since a reactive group can be placed at a specific position at the N-terminal or C-terminal (or less likely, but possible, central) part of the neck-region peptide. The molecules attached at these sites can be peptides or organic compounds.

Although the present invention is generally applicable, not all protein domains may be used with the neck region equally well. Very large domains may require specially adapted linker sequences and, most importantly, domains which show dimerizing or oligomerizing properties can form large aggregates which could be entirely insoluble or otherwise unsuitable for the use they were intended for. Also, the neck-region containing peptides should preferable be purified without the use of organic solvents such as acetonitrile used in reversed-phase chromatography. If used, for example after chemical synthesis, these compounds should be thoroughly removed since they can interfere with the trimerization. In a similar way, the presence during (hetero-) trimerization of sodium dodecylsulphate or similar, strong, ionic detergents should be avoided. (However, as these compounds disrupt the hydrophobic forces that hold the helices of the neck-region together they can, in a controlled way, be also useful reagents in the heterotrimerization at low temperatures.)

An amino acid sequence variant may comprise one or more changes, e.g. by way of addition, substitution, insertion or deletion of one or more amino acids, compared with wild type. Any such change should not abolish the ability of the polypeptide to form a trimer, though it may increase or decrease this ability depending on the nature of the change. A derivative has some modification compared to the naturally-occurring neck-region, which may be chemical. This may include the chemical or enzymatic attachment of carbohydrate structures, nucleic acids, or other chemical compounds, especially those used as antigen or those used in other chemical or biological interactions, such as ligand-receptor interactions.

Changes may be made to the amino acid sequence, compared with wild-type, by providing and manipulating suitable encoding nucleic acid used for the production of the polypeptide in an expression system. The present invention further provides nucleic acid comprising a sequence of nucleotides encoding a polypeptide able to form a trimer and comprising a neck-region of a collectin, an amino acid sequence variant thereof or derivative thereof, or a sequence of amino acids having an amino acid pattern and/or hydrophobicity profile the same as or similar to the neck region of collectin SP-D, fused to a heterologous sequence of amino acids, as disclosed herein.

The nucleic acid may comprise an appropriate regulatory sequence operably linked to the encoding sequence for expression of the polypeptide. Expression from the encoding sequence may be said to be under the control of the regulatory sequence.

Also provided by the present invention are a vector comprising nucleic acid as set out above, particularly any expression vector from which the encoded polypeptide can be expressed under appropriate conditions, and a host cell containing any such vector or nucleic acid.

A convenient way of producing a polypeptide according to the present invention is to express nucleic acid encoding it. Accordingly, the present invention also encompasses a method of making a polypeptide according to the present invention, the method comprising expression from nucleic acid encoding the polypeptide, either in vitro or in vivo. The nucleic acid may be part of an expression vector. Expression may conveniently be achieved by growing a host cell, containing appropriate nucleic acid, under conditions which cause or allow expression of the polypeptide.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells and many others. A common, preferred bacterial host is *E. coli.*

Suitable vectors can be chosen or constructed, containing appropriate regulatory sequences, including. promoter sequences, terminator fragments, polyadenylation sequences, enhancer sequences, marker genes and other sequences as appropriate. Vectors may be plasmids, viral e.g. 'phage, or phagemid, as appropriate. For further details see, for example, *Molecular Cloning: a Laboratory Manual:* 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology,* Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage.

The introduction may be followed by causing or allowing expression from the nucleic acid, e.g. by culturing host cells under conditions for expression of the gene.

In one embodiment, the nucleic acid of the invention is integrated into the genome (e.g. chromosome) of a host cell. Integration may be promoted by inclusion of sequences which promote recombination with the genome, in accordance with standard techniques.

Following expression, polypeptides may be caused or allowed to trimerise. This may be prior to or following isolation.

The tightly associated trimer of α-helices found at the neck-region of SP-D is, to our knowledge, the first example of a self-assembling structural motif, C-terminal to a collagen triple-helical structure, which does not involve the formation of disulphide bridges. Also, our findings demonstrate (see example 1) that, although collagenous sequences of repeating Gly-Xaa-Yaa triplets require additional protein sequences for inter-chain recognition, and association at their C-terminal ends, to initiate folding to an intact triple-helix, this association itself does not have to be in a staggered fashion in order to align the three chains in the correct register to form the staggered collagen helix. It seems, too, that the present invention may have advantages over prior art multimerising peptides which form dimers and tetramers in addition to trimers.

The small size of this self-assembling domain as well as the lack of the requirement for disulphide bridges will allow particularly for the use of a "neck-region" peptide in the association and registered alignment of any collagenous polypeptide sequence, composed of Gly-Xaa-Yaa triplets, irrespective of the origin of that collagenous sequence. It is feasible to use a neck-region peptide at the C-terminus of any collagenous polypeptide sequence to initiate the formation of collagen triple-helical conformation of the Gly-Xaa-Yaa triplets [3]. However, the stability of collagenous structure also depends on the number of the triplets and the nature of the peptide structure at the N-terminal end of the triple-helical region. Also, the hydroxylation of proline residues in Yaa position has been shown to greatly enhance stability of the triple-helix [24]. Use of the neck-region peptide to initiate triple-helix formation enables the relative importance of these factors influencing the stability of collagenous structure to be analysed.

The present invention thus also provides the use of a polypeptide comprising or consisting essentially of the neck-region of a collectin, or an amino acid sequence variant thereof or derivative thereof, in a method of "seeding" of a collagenous triple-helix. Preferably, the polypeptide consists essentially of a series of collagenous triplets (Gly-Xaa-Yaa) fused at the C-terminus (possibly via a linker) to the "neck-region" of a collectin or amino acid sequence variant thereof or derivative thereof, or a sequence of amino acids having an amino acid pattern and/or hydrophobicity profile the same as or similar to the neck-region of collectin SP-D, with no amino acids C-terminal to the neck-region or heterologous amino acids C-terminal to the neck region. The "neck-region" (i.e. "first sequence of amino acids" as disclosed herein) may be at the C-terminus of the polypeptide, or there may be additional C-terminal amino acids, the proviso being that the polypeptide as a whole is non-naturally occurring.

A method of seeding a collagenous triple-helix involves causing or allowing trimerization of such a polypeptide. It may involve first the production of the polypeptide by expression from encoding nucleic acid therefor. The present invention provides such nucleic acid, a vector comprising such nucleic acid, including an expression vector from which the polypeptide may be expressed, and a host cell transfected with such a vector or nucleic acid. The production of the polypeptide may involve growing a host cell containing nucleic acid encoding the polypeptide under conditions in which the polypeptide is expressed. Systems for cloning and expression etc. are discussed supra.

Trimerization may be followed by isolation of trimers, e.g. for subsequent use and/or manipulation.

As demonstrated experimentally herein neck-region peptide may be used to generate polypeptides with one or more amino acids carrying distinct properties, at either end of the neck-region, and, using hetero-trimerization, these properties can be combined with those carried by other domains in separately generated polypeptides containing the neck region.

For example, a single-chain antibody may be trimerized by generating it as a fusion polypeptide with the neck-region in an expression system. Fusion of antibodies or fragments thereof, including scFv, may be directed against cell-surface molecules, such as CD8, CD4 or TCRδ, for instance. Trimeric molecules should have a higher avidity to their respective ligands than the monomeric forms without the neck-region. Using a mild heterotrimerization technique of heating (e.g. to about 50° C.) and cooling (e.g. ambient temperature) individual trimers may be dissociated and re-associated to yield heterotrimeric complexes. These complexes may carry a weaker affinity for each individual ligand, but a strong avidity for an entity displaying two or more of the respective ligands. For example, trimerised anti-CD4, anti-CD8 and anti γδ TCR scFv molecules would have strong affinity for an entity which is CD4, CD8 and γδ TCR positive. Thus, heterotrimers may be created with molecules with any combination of first, second and third binding specificities.

Where specific recognition only involves one end, e.g. the C-terminal end, of the neck-region in the polypeptides, the other, e.g. N-terminal end, of the neck-region may be used for additional functions, e.g. in drug targeting or diagnostic detection.

Further applications of homo- or heterotrimerizations may include use of any of the following:

(i) peptide-ligands for receptors, especially low-affinity binding (e.g. neuropeptides, interleukins).

(ii) antigens.

(iii) chemical compounds that are reactive upon activation e.g. photo-activatable chemical crosslinkers that react with any molecule such as a protein, either specifically or generally, when close by. The neck-region peptide may be part of a trimer carrying a ligand with specificity for an unknown receptor; after specific binding to the receptor the crosslinker may be UV-activated and only molecules close to the ligand-receptor complex could be crosslinked and thus identified.

(iv) organic compounds e.g. caffeine, morphine (e.g. for research, diagnostic, or therapeutic use).

(v) low affinity binding domains especially for the screening of potential inhibitors in pharmaceutical research.

(vi) indicator molecules for pH, $CaCl_2$ concentration or others relevant to diagnostics and research.

(vii) carbohydrate binding domains.

(viii) carbohydrates e.g. for binding and/or research on lectins.

(ix) lipid-containing structures (these may be at the N-terminal end for incorporation into liposomes, e.g. containing an active molecule, and the trimerising polypeptides may have a specificity directing domain at an end, e.g. the C-terminal end, of the neck-region.

(x) DNA or RNA or derivatives (this may be useful when more than one protein shall be directed to act at a specific site in e.g. a chromosome, or when simple chemical attachment of DNA to that effector enzyme affects its function. If the DNA-DNA interaction (DNA at one end of the neck-region and DNA in the chromosome) has a higher dissociation temperature than the neck-region peptide (which is very likely) then different functional polypeptides may be added subsequent to the initial DNA recognition. This may be used in a similar fashion as in-situ hybridizations, where a fluorescent tag is added to the oligonucleotide, allowing the position of a gene on a chromosome to be visualized in the microscope. The neck-region DNA probe may therefore be hybridized to, e.g., the human chromosome at the position of a given gene at usually about 65–75° C. The solution may then be cooled to about 50° C. and unhybridized probes may be washed away. Then, still at about 50° C., another neck-region polypeptide may be added, containing, for example, a DNA-cleaving polypeptide that would cleave anywhere if brought to suitable conditions e.g. addition of ATP and S-adenosylmethionine. The soluble, added, neck-region enzyme fusion protein and the 'immobilized' DNA-neck-region molecules may then allowed to heterotrimerize by cooling the solution, and after sufficient washing, the co-factors may be added. Now the enzyme would be active but would only cleave at the site of the hybridization. This is extremely useful, especially if the enzyme in question cannot stand the temperatures required to perform the DNA-DNA hybridization, but retains its activity when mildly heterotrimerized. Alternatively, the second neck-region fusion protein may (also) contain a purification-tag for the isolation of DNA that contains a specific DNA sequence. The system of specific DNA recognition with the delayed delivery to that recognized site of a functional protein domain may be used in other circumstances, such as in-situ hybridizations, genomic library construction (Human Genome Project), in-vitro assays, or non-radioactive diagnostics.

(xi) the neck-region may be attached to a solid matrix (this may be useful e.g. as a research tool to reversibly immobilize recombinant proteins which contain the neck-region). Resin with the immobilized (preferably via N-terminus) neck-region may be mixed at about 25° C. at sub-physiological ionic strength with a recombinant neck-region fusion polypeptide e.g. containing a single-chain antibody, and heterotrimerized. Two single-chain antibody molecules may be bound per neck-region molecule on the resin, and oriented towards the solvent. The resin may then be used like a normal affinity matrix, but may be used again for a different molecule by releasing the single-chain antibody neck-polypeptides, for instance at about 50° C. and recharging with a new neck-region peptide-containing molecule.)

(xii) enzymes (especially enzymes of the same reaction pathway that are subsequently involved, such that the product of one reaction is the substrate for the next enzyme). The close location of the enzymes may bring advantages due to short diffusion way and therefore the reduced likelihood of side-reactions. Also, the immobilization of the enzymes via the neck-region of one of the three polypeptide chains may bring advantages, such as the easy removal of the enzymes or the reaction on a column. This advantage may also be gained by a heterotrimeric or homotrimeric enzyme complex that may be removed from the rest of the solution by mixing it with an excess of neck-region-resin at about 50° C., cooling, and removal of the resin. Applications may include the enzymes used in molecular biology, because the substrates and products of their actions are mainly DNA molecules which are very (thermo) stable.

(xiii) cysteine residues may be added to either end or both ends of the sequence in order to generate a covalently linked trimer. The exact sequence containing the cysteines may be derived from the FACIT collagens, some of which are linked into trimers via disulphides immediately following the collagenous structure, thus allowing for a transfer of one of those sequences to the N-terminus of the neck-region. This may be of use to further increase the stability of the peptide timer without affecting the overall shape.

The present invention will now be illustrated further by way of example and with reference to the following figures.

FIG. 1(a) schematic drawing of the location of the neck-region peptide of human SP-D. Human SP-D consists of 12 identical polypeptide chains (each of 356 amino acids) which assemble into 4 rod-like structures, each composed of three chains, which form triple-helical collagenous structures over residues 26–202. The C-terminal ends of the molecule contain C-type lectin domains linked to the collagenous domains via the neck-region, whereas the N-terminus is involved in oligomerization of the trimers into a tetramer. The position of the neck-region within the human SP-D protein and the sequence of the neck-region peptide as expressed in Example 1. The 'a' and 'd' positions of the α-helical coiled-coil are indicated. (SEQ ID NO:7)(b) a-helical wheel drawing of the neck-region peptide. The drawing is down the helical axis beginning at the N-terminal valine residue at the 'a' position.

FIG. 2 shows circular dichroism spectroscopy analysis of the thermal stability of the secondary structure of the collagenase-digested neck-region peptide. Quarz cuvettes containing the peptide solution (adjusted to give an OD reading at 210 nm of 1.0) were allowed to equilibrate for 15 min at each temperature selected. Circular dichroism spectroscopy profile of the collagenase-digested (dashed line) and the intact neck-region peptide, collected at 20° C., with both peptides in 30 mM phosphate buffer pH 7.4, adjusted to give an UV absorption of 1.0 at 210 nm. The blank baseline was subtracted for both peptides and the resulting curves were overlaid. The spectra are almost identical and show a negative value of approximately −30 mdeg at the wavelength 207 nm, and of approximately −20 mdeg at the wavelength 224 nm, which is in good agreement with spectra expected from α-helical structures. 2(b): The curve shows a thermal transition at approximately 55° C. However, this transition occurs over a wide range of temperatures and more experimental data will be required to establish a more precise melting temperature for the neck-region peptide.

Figure 4:
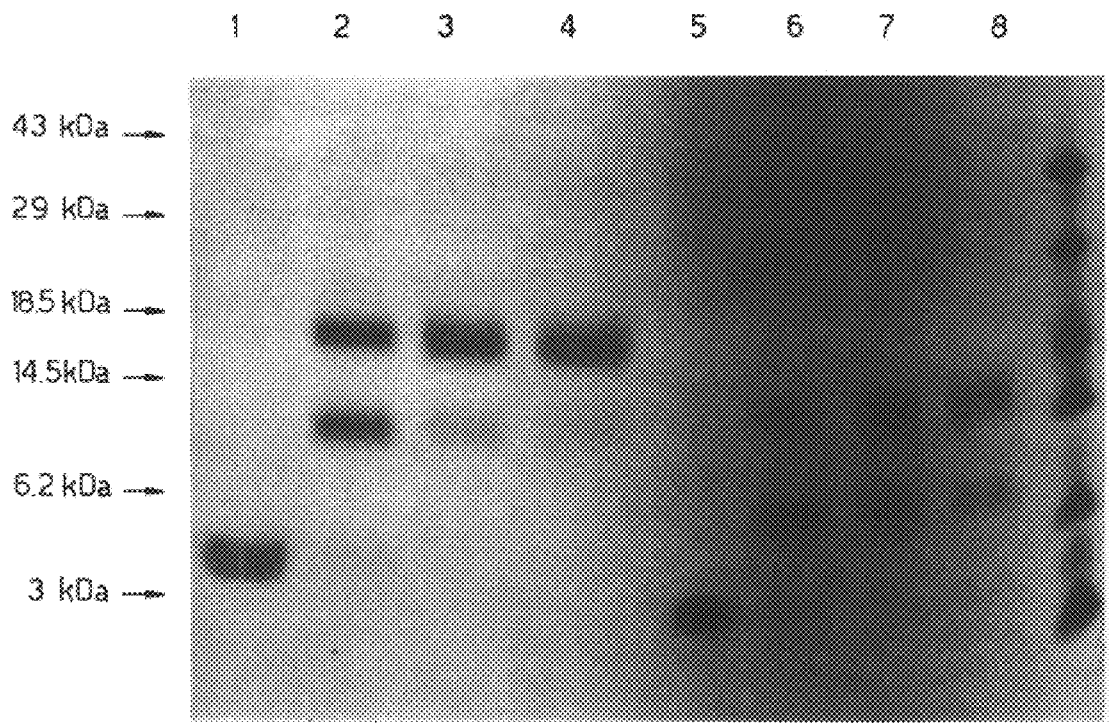

FIG. 4 shows SDS-PAGE analysis (Coomassie Blue R-250 stain of a 15% (w/v) acrylamide tris-tricine-glycerol gel) of the purified collagenase-digested (lanes 5–8) and the intact neck-region peptides (lanes 1–4), reacted with increasing amounts of Bis-(sulphosuccinimidyl)-suberate. 0 mM (lanes 1 and 5), 3 mM (lanes 2 and 6), 5 mM (lanes 3 and 7), and 10 mM (lanes 4 and 8) of crosslinker were incubated for 20 min at 37° C. with a constant (10 μg) amount of peptide in 40 μl PBS before the samples were boiled in Tris-containing SDS-PAGE loading buffer, stopping the reaction. Both peptides can be crosslinked into their respective trimeric complexes without the appearance of higher-order aggregates. The trimer of the collagenase-digested peptide runs at approximately 16 kDa, whereas the neck-region peptide trimer shows a molecular weight of approximately 22 kDa.

Figure 6:
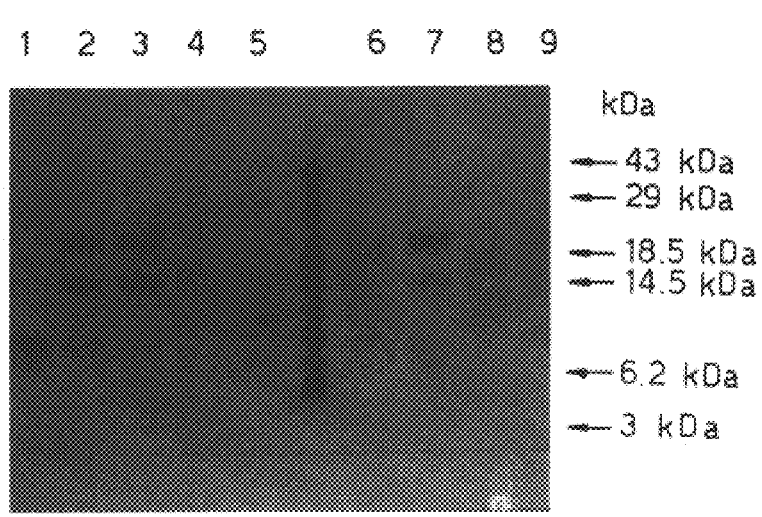
Figure 5:
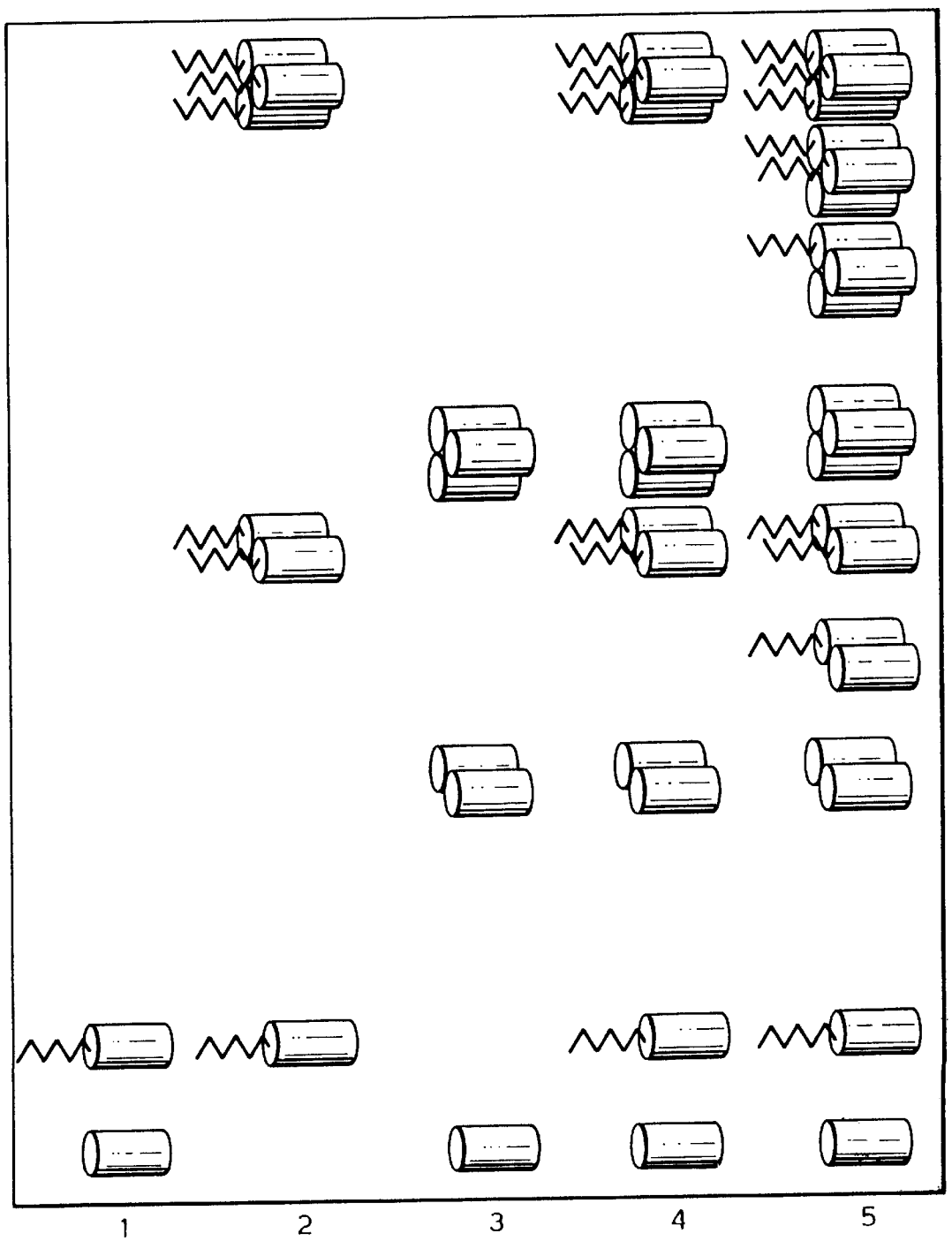

FIG. 5 shows a schematic representation of a crosslinking experiment, analysed by SDS-PAGE (see FIG. 6). The drawing in lane 1 show the un-crosslinked single polypeptide chains of both, the collagenase-digested and the intact neck-region peptide. Lane 2–5 represent crosslinking reactions, with lane 2 showing the neck-region peptide analysed after a partial crosslinking reaction, showing monomeric, dimeric, and trimeric molecular weights. Lane 3 represents the same analysis for the collagenase-digested peptide, and lane 4 indicated the expected result of a crosslinking reaction of both peptides when the solution is not heated and cooled before the crosslinking step. If the heating and cooling is carried out before the crosslinking reaction, heterotrimeric complexes should be detectable, showing intermediate molecular weights, as indicated in lane 5.

FIG. 6 shows SDS-PAGE analysis (Coomassie Blue R-250 stain of a 15% (w/v) acrylamide tris-tricine-glycerol gel) of the purified collagenase-digested and the intact neck-region peptides, involving crosslinked of the individual peptides following heating and cooling steps in PBS, and mixing of the two peptide species in different ratios (before heating and cooling) followed by crosslinking. Lane 1 shows both, the collagenase-digested and the intact neck-region peptide, 1 and 5 µg respectively, without crosslinker added. The neck-region peptide reacted with 5 mM Bis-(sulphosuccinimidyl)-suberate is shown in lanes 2 and 3, with the peptide solution incubated at 99° C. for 20 min followed by chilling on ice before addition of crosslinker shown in lane 3. The same reactions with the collagenase-digested peptide are shown in lanes 4 and 5, respectively. Peptides in lanes 3 and 5 were subjected to heating and cooling. In lanes 6–9 different amounts of the two peptides were mixed prior to heating and cooling, followed by crosslinking with 5 mM crosslinker. The ratios (neck-region peptide:digested peptide) are 1:1 in lane 6, 4:1 in lane 7, 1:4 in lane 8, and 2:1 in lane 9. The banding pattern indicates that firstly the heating and cooling did not alter the detection by crosslinking of a trimeric complex, secondly, as mixed complexes can be crosslinked, that the polypeptides of different complexes are dissociated at high temperatures and that they re-anneal in mixed complexes, and thirdly, that these hetero-trimerizing reactions can be driven in a concentration-dependent manner.

Figures 7A, 7B:
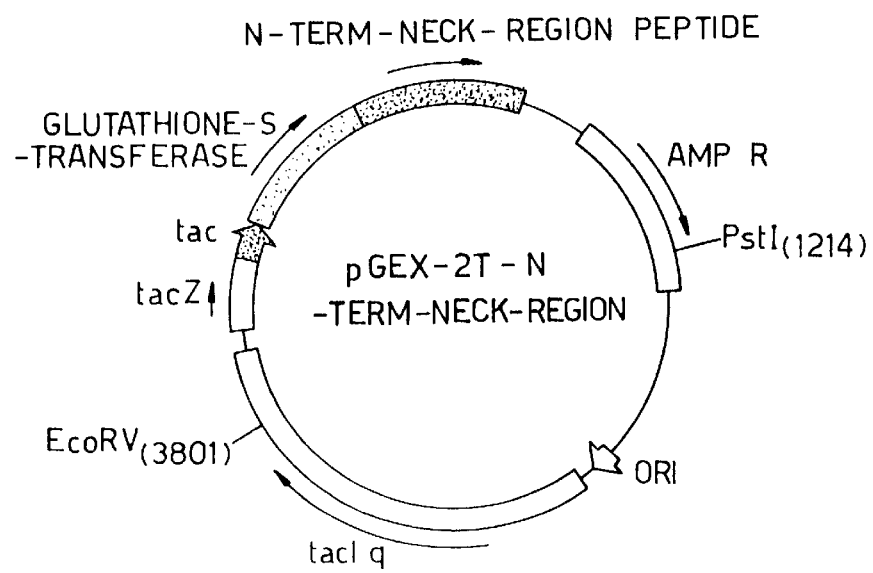

FIGS. 7(a) and 7(b): The pGEX-2T-N-term-neck-region plasmid allows for the induction (with IPTG) of a glutathione-S-transferase-N-terminus-neck-region fusion protein which can be cleaved with thrombin to yield the peptide sequence shown. (FIG. 7(a)) (Lower case indicates pGEX polylinker sequence and the N-terminus sequence is underlined.) The DNA construct was obtained by Sma1 and Nru1 digestion of the pGEX-2T-N-term-coll-neck-region plasmid (FIG. 7(b)) and subsequent religation of the compatible sites. (SEQ ID NO:9 and SEQ ID NO:10)

Figure 8:
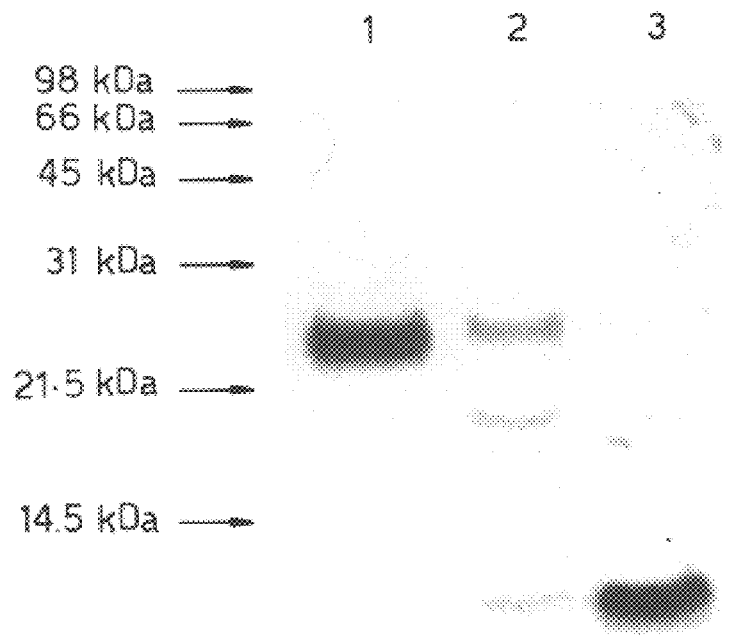

FIG. 8 shows SDS-PAGE analysis (Coomassie Blue R-250 stain of a 15% (w/v) acrylamide gel) of the purified N-term-neck-region fusion peptide, reacted with increasing amounts of crosslinker, under reducing (lanes 4,5,6) and non-reducing (lanes 1,2,3) conditions. Peptides (50 µl) were incubated with 0 mM (lanes 3 and 6), 2 mM (lanes 2 and 5), and 5 mM (lanes 1 and 4) Bis-(sulphosuccinimidyl)-suberate in PBS for 20 min before 10 µl 1 M Tris.Cl pH 8.0 was added to quench the reaction. When the reaction went almost to completion a protein species of approximately 29 kDa can be detected, whereas bands corresponding to dimeric (approximately 19 kDa) and single chain N-term-neck-region peptide (9 kDa) were detected in incompletely or non-crosslinked reactions. Under non-reducing conditions approximately half of the peptide runs as a dimer, and increased amounts of dimers and trimers are seen compared to the reduced samples, in the crosslinking reactions.

Figure 9A:
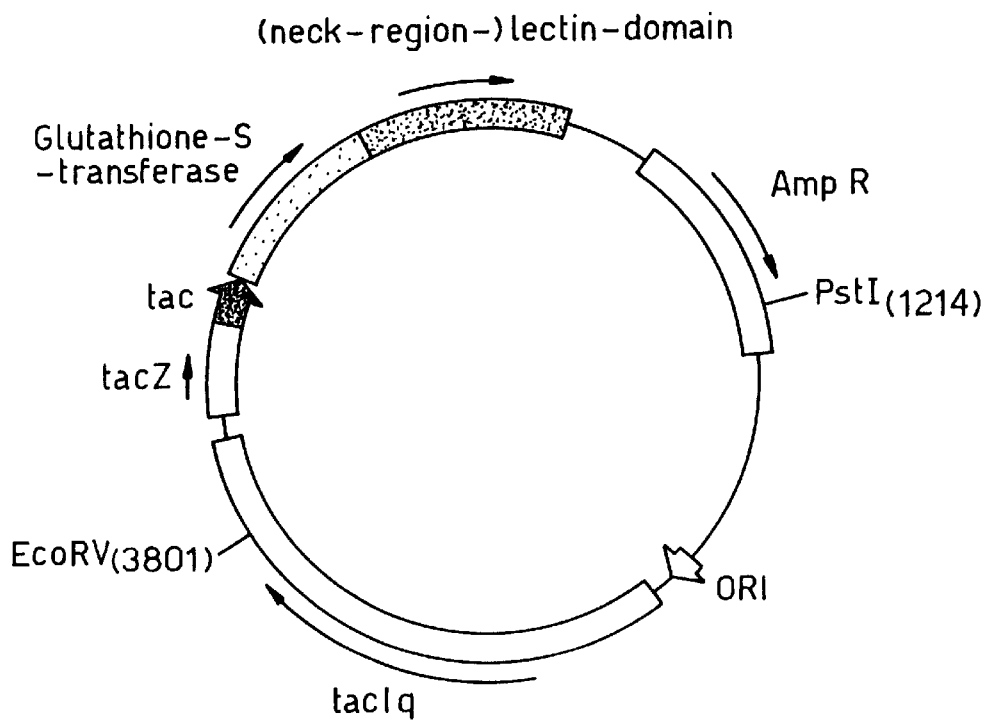
Figure 9B:
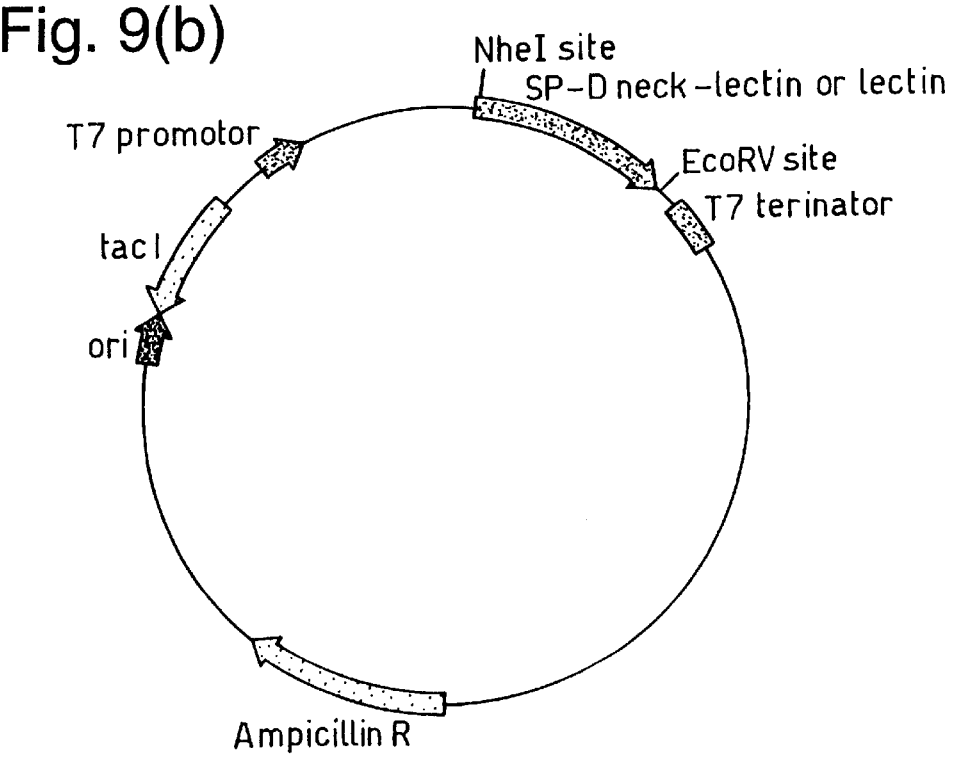

FIG. 9 illustrates transfer of the neck-region-lectin and -lectin coding DNA fragments from the fusion protein generating pGEX-2T system (a) to the pET3a vector. The DNA fragments were excised using BamH1 and EcoR1 and subcloned into the pBluescript plasmid, which was linearized by using the same enzymes. After repurification of the resulting plasmids from transfected NM554 cells the DNA fragments were excised using Xba1 and EcoRV, thus generating compatible ends to the sites present in the pET3a plasmid cut with Nhe1 and EcoRV. The Nhe1 site is positioned at the start codon of the pET3a open reading frame. Therefore the proteins induced will not carry a fusion partner at the N-terminal end of their sequence, but only 7 amino acid derived from the pBluescript polylinker sequence: MARTSGS (SEQ ID NO:11).

FIG. 10 shows SDS-PAGE analysis (Coomassie Blue R-250 stain of a 12.5% (w/v) acrylamide gel) of the C-type lectin domain of human SP-D and the neck-region-lectin domain as purified from lysates of bacterial cultures induced to express the recombinant proteins using the pET-3a vector. Lanes 1 to 3 correspond to the lectin domain, and lanes 4–6 show the neck-region-lectin domain protein. The proteins were crosslinked using increasing final concentrations of Bis-(sulphosuccinimidyl)-suberate. Reactions of lanes 1 and 4 contain 0 mM, lanes 2 and 5 correspond to 5 mM, and lanes 3 and 6 show the result of reactions with 10 mM crosslinker. Although the neck-region-containing protein can be shown to consist of trimers that can be crosslinked, no such crosslinkable oligomers exist for the lectin domain expressed on its own. Thus, the neck-region can mediate trimerization whereas no self-associating properties could be detected for the lectin domain of human SP-D alone.

FIG. 11: illustrates (a) size-exclusion chromatography of the neck-region peptide/neck-lectin protein before (A) and after heterotrimerization (B) using a Superose 12 column. The column was equilibrated and run in PBS at 0.3 ml/min and the UV detector was set at 280 nm (sensitivity of 0.02). Samples were injected using 100 ml loops. The neck-lectin trimeric complex elutes first, with the neck-region peptide trimer following. After heterotrimerization a shift in the elution profile of the first peak can be detected corresponding to trimeric protein complexes consisting of 2 neck-region peptides and 1 neck-lectin protein. (b) shows a schematic representation of the heterotrimerization process. The different polypeptides containing the neck-region are forming heterotrimers after a re-annealing step and this is a concentration-driven process with the relative amounts of the two homotrimeric molecules used at the beginning determining the ratios of the products of the heterotrimerization reaction.

FIG. 12: The pGEX-2T-N-term-coll-neck-region plasmid (B) allows for the induction (with IPTG) of a glutathione-S-transferase-N-terminus-coll-neck-region fusion protein which can be cleaved with thrombin to yield the 25 kDa SP-D polypeptide. The DNA construct was obtained by PCR using a 5' oligonuclotide introducing a BamH1 site at the start of the N-terminal sequence and a 3' oligonucleotide introducing an EcoR1 site after the stop codon of the SP-D cDNA as primers, thus amplifying a DNA fragment coding for the entire protein sequence of the native SP-D protein (A). Subsequently, the PCR product was cloned into pBluescript using the engineered enzyme sites and the resulting plasmid was digested with the restriction enzymes BamH1 and Msc1 and the DNA fragment coding for the N-tem-coll-neck-region was cloned into the pGEX-2T plasmid, linearized with BamH1 and Sma1.

Figure 13:
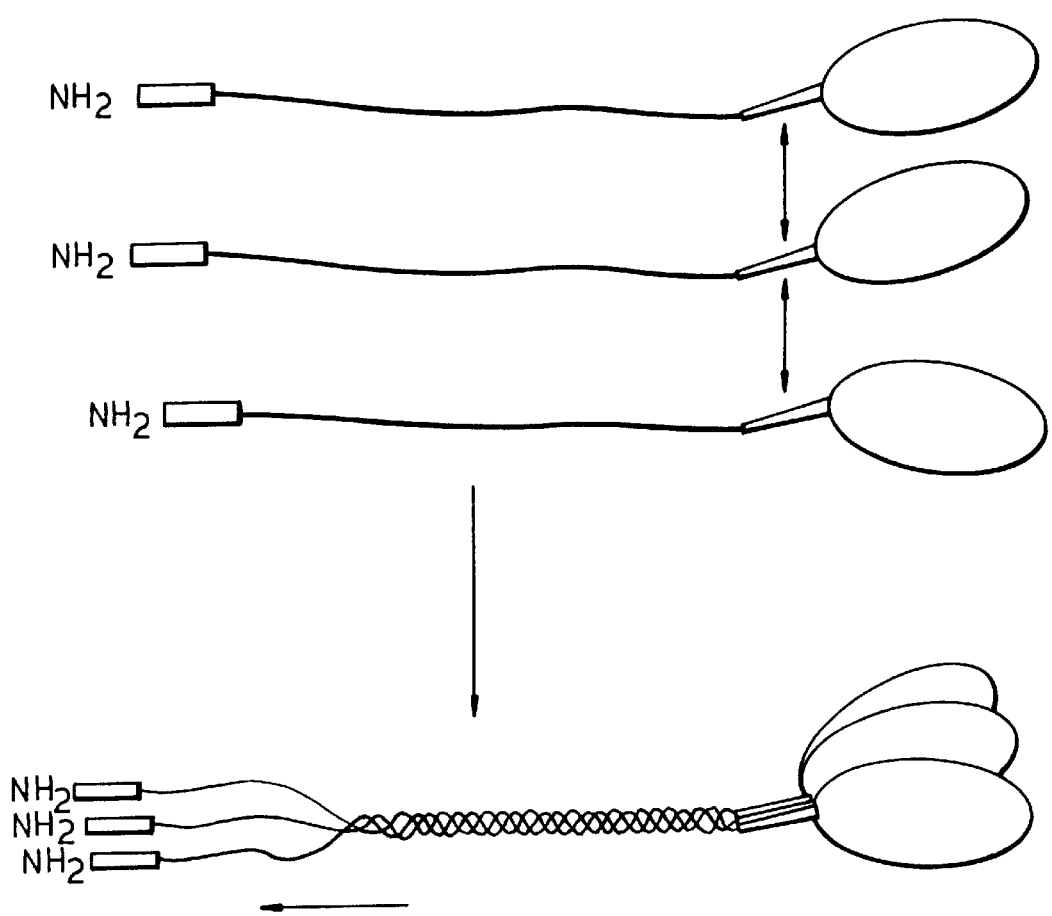

FIG. 13 shows a schematic representation of the proposed folding process involved in the formation of the triple-helical collagen-like region of human SP-D. The neck-region associates as a parallel homotrimeric coiled-coil and provides thus a nucleation point for the formation of the triple-helical structure in the adjacent collagenous region. The collagen triple-helix forms in a zipper-like fashion from this nucleation point towards the N-terminal end of the polypeptide chain. There are numerous potential cleavage sites for Thrombin present within the collagenous sequence, however, the formation of a triple-helix would render these sites resistant to proteolytic digestion because the only known proteases to be able to digest collagenous structures are collagenases.

Figure 14:
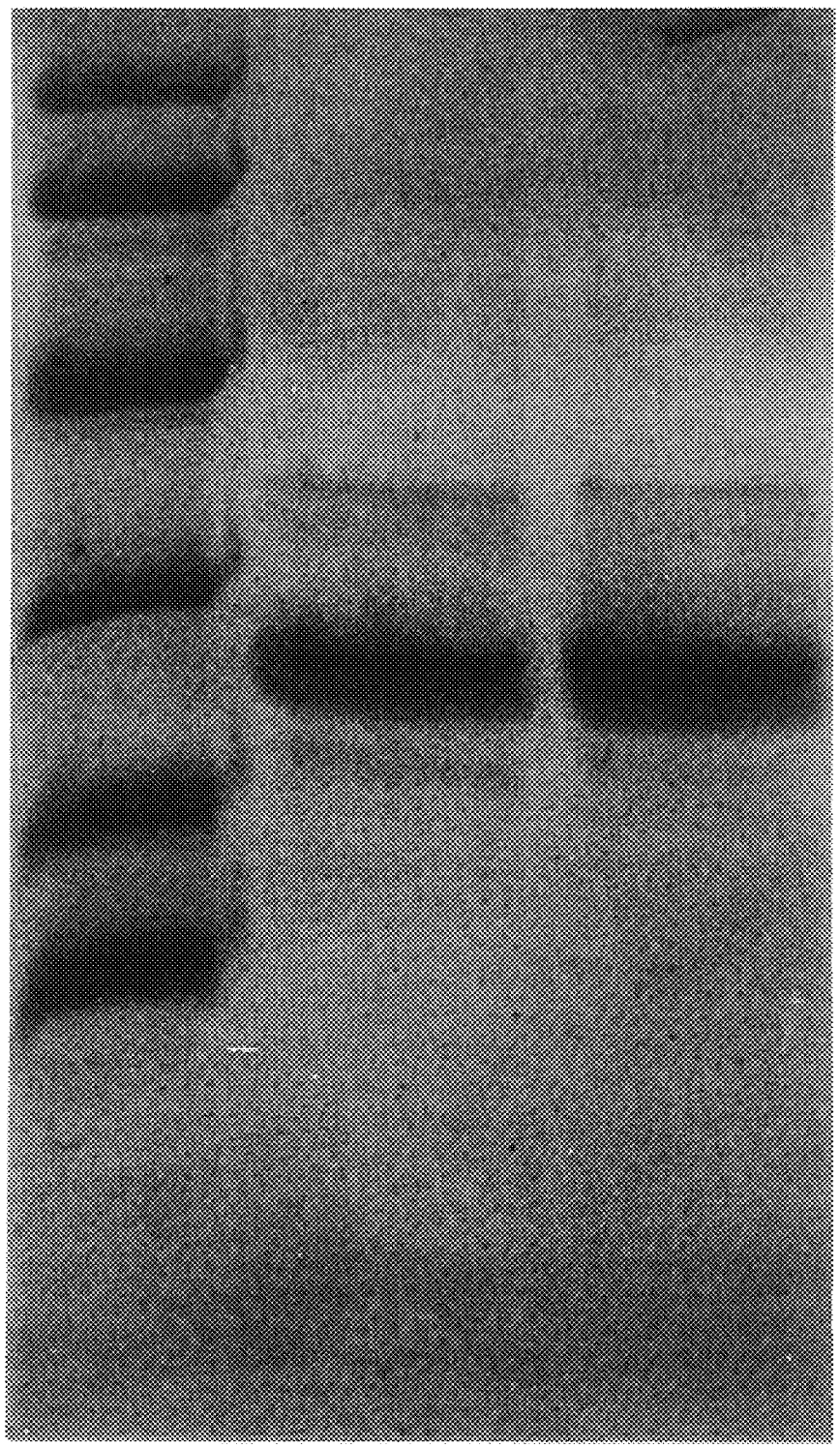

FIG. 14 shows (a) SDS-PAGE analysis (Coomassie Blue R-250 stain) of the Glutathione-S-transferase-N-term-collagen-neck-region fusion protein before and after thrombin cleavage (10 % (w/v) acrylamide). 50 μl solution of the eluted and glycine-treated fusion protein were loaded before (lanes 1,2) and after thrombin digestion (Lanes 3–6). The close-up of lanes 5&6 (b) shows the less-intensely stained 25 kDa recombinant peptide running underneath the 25 kDa glutathione-S-transferase band.

Figure 15:
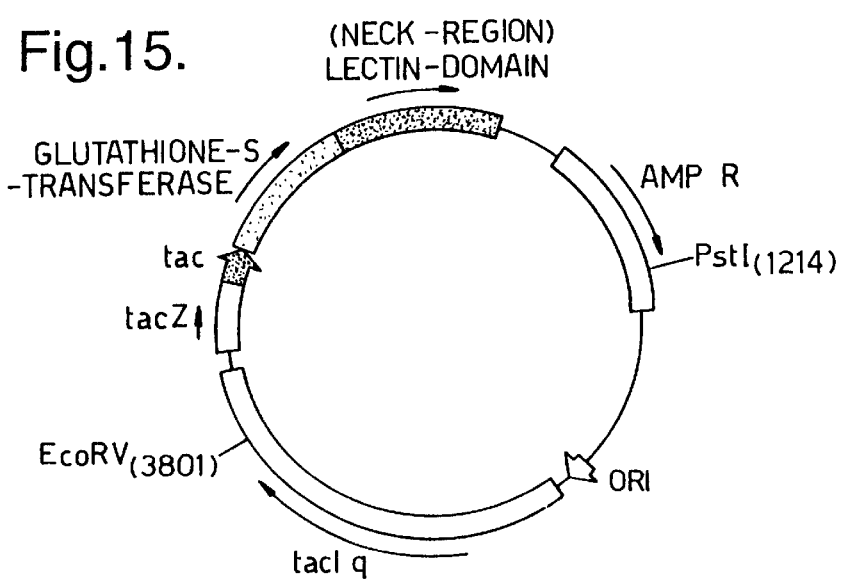

FIG. 15: The pGEX-2T-neck-region-lectin and pGEX-2T-lectin plasmids were generated using either Sma1 and EcoR1 (neck+lectin) or Msc1 and EcoR1 (lectin) to clone the SP-D cDNA fragments into the pGEX-2T plasmid, linearized with Sma1 and EcoR1. The fusion proteins induced are 43 kDa (neck+lectin) and 37 kDa (lectin) in expected molecular weight.

Figure 16:
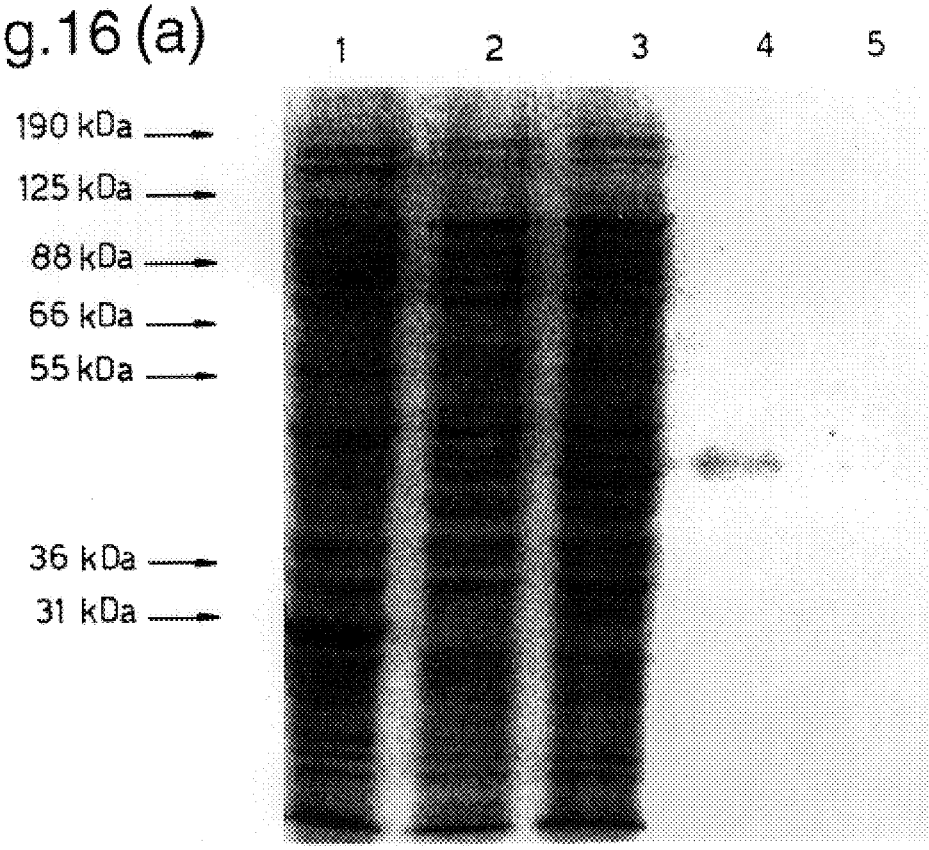
Figure 16:
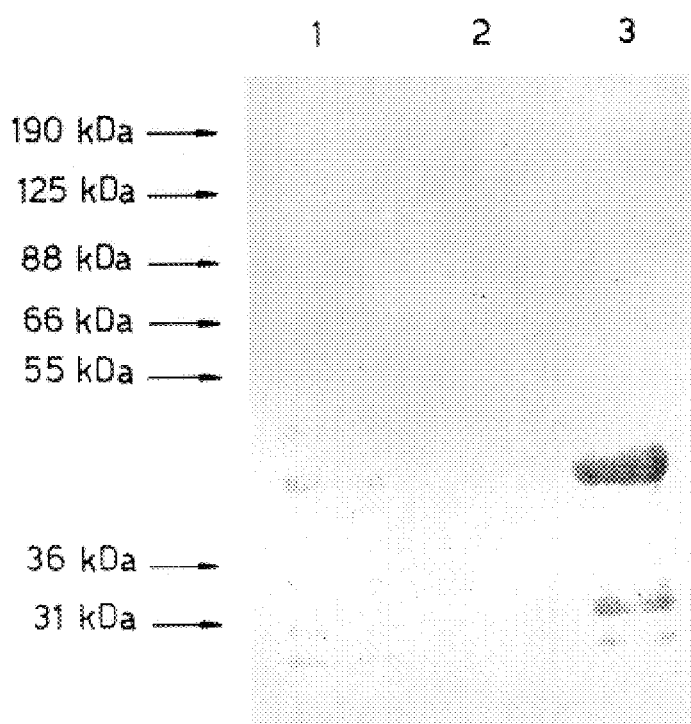

FIG. 16 shows SDS-PAGE analysis (10% (w/v) acrylamide gel) of bacterial expression of the glutathione-S-transferase fusion proteins containing the neck-region and the lectin region (A) and the lectin domain of human SP-D alone (B). Non-induced (A lanes 2 and 3, and B lanes 1 and 2) and induced bacteria (A lane 1 and B lane 3) were boiled and loaded onto the gels, run under reducing conditions. Protein bound to maltose-TSK was eluted using EDTA, and peak samples (50 μl) loaded onto lanes 4 and 5, no protein eluted for the glutathione-S-transferase-Lec fusion protein. The fusion protein containing both the neck-region as well as the lectin domain appears to be susceptible to proteolytic degradation within the cells, for a prominent protein band in lane A 1 is not only present at the expected size of approximately 42 kDa, but also at approximately 30 kDa. However, this protein did not bind to the maltose-TSK column. The glutathione-S-transferase-Lec fusion protein showed a molecular weight of approximately 37 kDa.

Figure 17A:
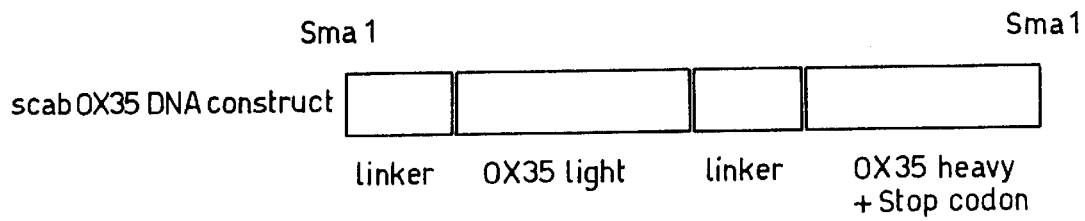
Figure 17B:
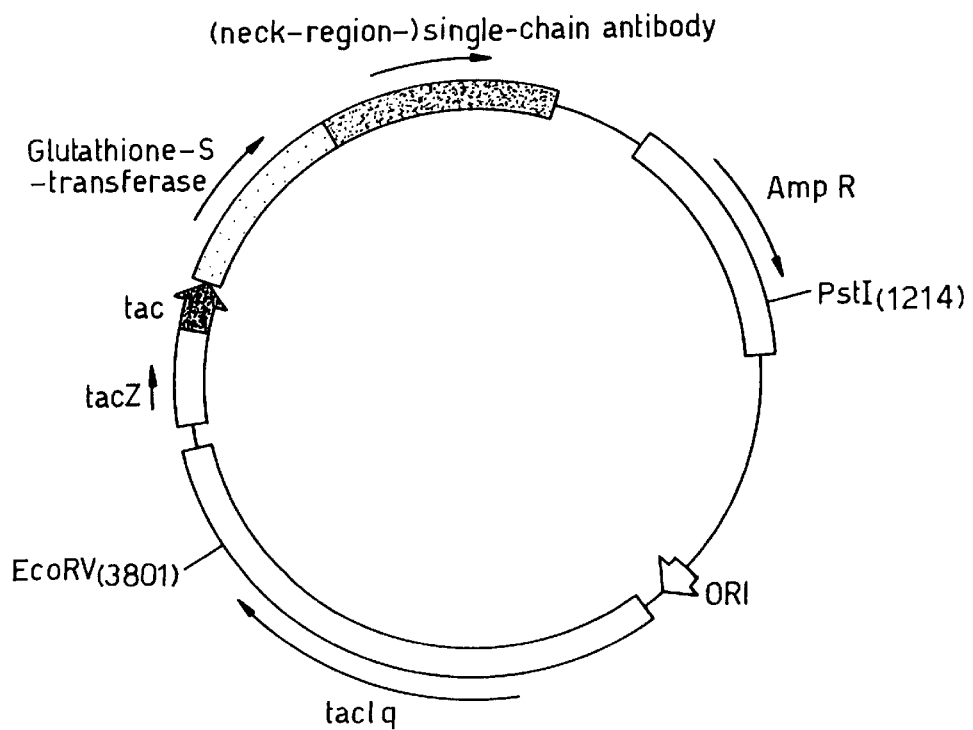

FIG. 17 shows a DNA construct encoding the immunoglobulin domains of the variable regions of the monoclonal rat anti-CD4 IgG antibody heavy and light chains (scabOX35), fused together by a flexible linker sequence (a). The DNA fragment was inserted into the Sma1 site of the pGEX-2T-neck-region peptide, resulting in an open reading frame for a fusion protein with the glutathione-S-transferase and the neck-region. The DNA was also inserted into the pGEX-2T plasmid (b), linearized with Sma1, thus producing a fusion protein of scabOX35 with glutathione-S-transferase alone.

Figure 18:
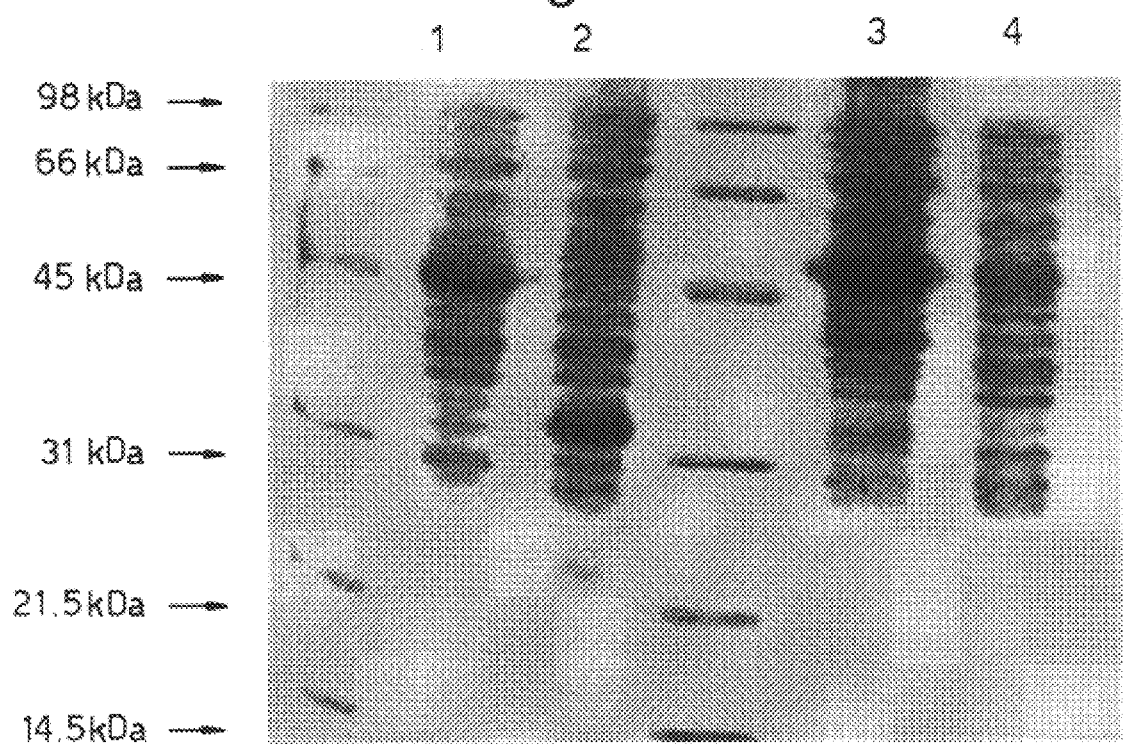

FIG. 18 shows SDS-PAGE analysis (Coomassie Blue R-250 stain) of bacterial lysates of cultures induced to express glutathione-S-transferase fusion proteins with the OX35-single-chain antibody (lane 1) the neck-region of human SP-D (lane 2), and the neck-region-OX35-single-chain antibody (lane 3), compared to non-induced bacteria (lane 4), under reducing conditions (12.5% (w/v) acrylamide).

All documents mentioned in the text are incorporated herein by reference.

EXAMPLE 1

Trimerisation of a Collectin Neck Region

FIG. 1(a) shows the structure of human SP-D. A 168 bp DNA fragment, which encoded 7 Gly-Xaa-Yaa triplets and the 35 non-collagen like residues of the neck-region leading up to the C-type lectin domain. It was cloned into the pGEX-2T bacterial expression vector [9] and the correct orientation of the insert was checked by restriction digestion. High levels of expression of the glutathione-S-transferase/neck-region peptide fusion-protein were obtained after 6 hours of induction with IPTG. Thrombin digestion of the affinity purified fusion-protein resulted in two polypeptides, the glutathion-S-transferase and the neck-region peptide, carrying an additional Gly-Ser-Pro triplet at the N-terminus and the residues Gly-Ile-Pro-His-Arg-Asp (SEQ ID NO:12) at the C-terminal end, representing the polylinker present in pGex-2T. 14 mg of the recombinant peptide were purified per liter culture in the three-step purification procedure. The peptide elutes in a single peak from the HighLoad-S column, at 800 mM NaCl. The purity of the peptide was confirmed by SDS-PAGE analysis, N-terminal sequencing of residues 1–46, and laser desorption mass spectroscopy (data not shown).

Figure 2A:
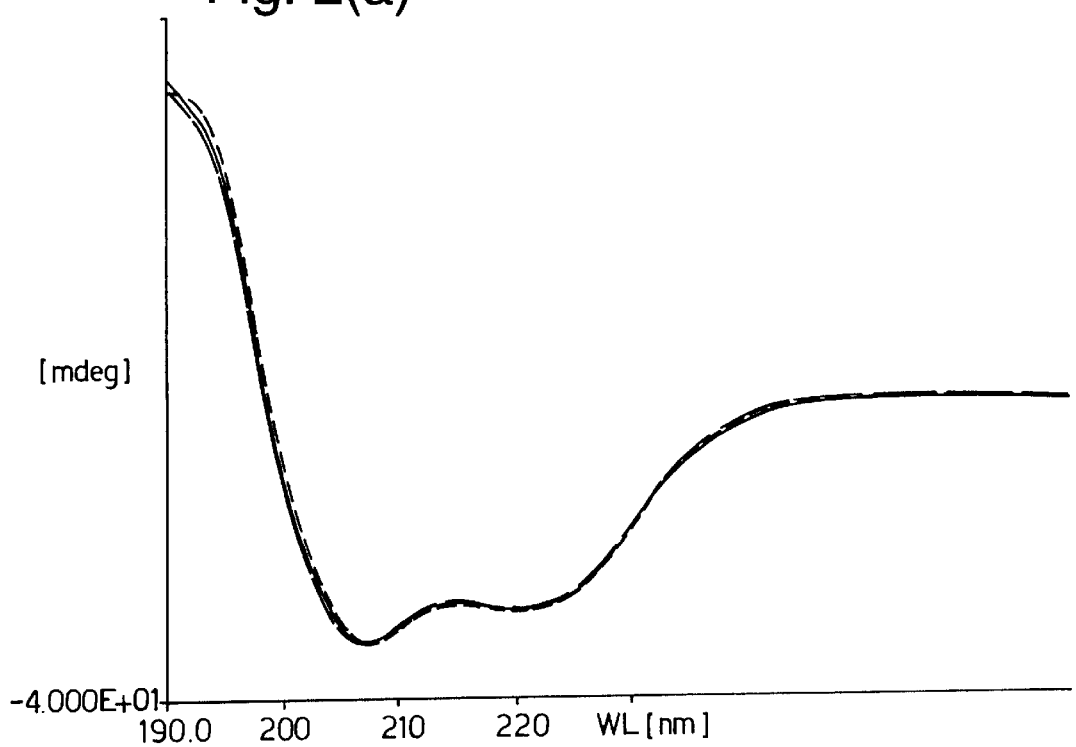
Figure 2B:
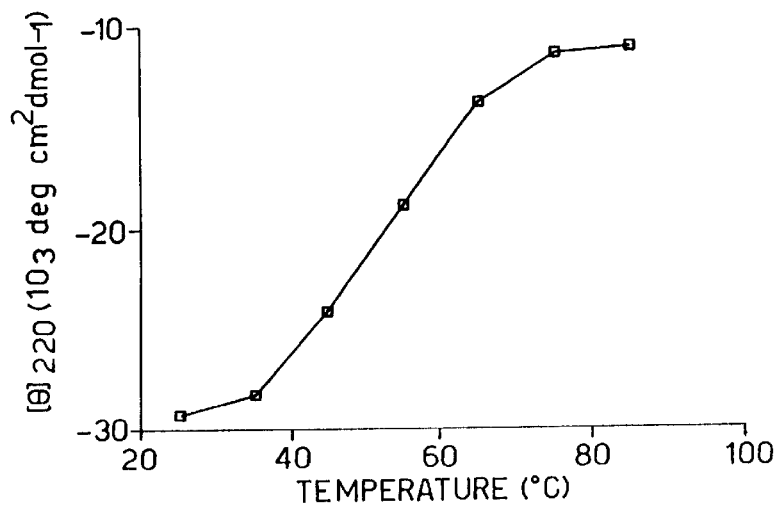

To determine the secondary structure of the peptide, far-ultraviolet CD measurements were carried out on the collagenase-treated neck-peptide (FIG. 2(a)). The spectra show a strong positive value at 193 nm with two negative values at 208 and 223 nm, consistent with the expected profile of α-helical structure [10]. The structure disappears reversibly with increasing temperature and a thermal unfolding transition at 55° C. was observed.

As the location of the neck-region within the SP-D protein suggests a parallel orientation of the α-helices and the amino acid sequence of the peptide contains hydrophobic residues, in a repeating heptad pattern, the three α-helices could associate in a coiled-coil with the hydrophobic residues forming the interface between the helices (FIG. 1(b)) [11].

Figure 3B:
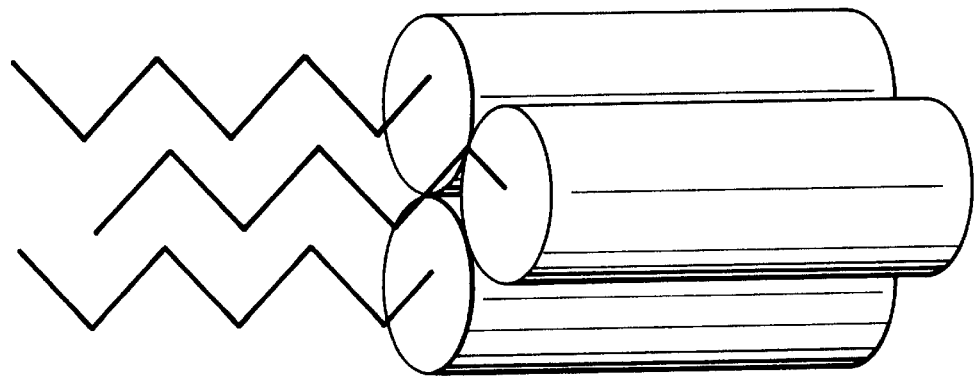
FIG. 3(b) shows a schematic representation of trimerised neck region peptides (tubes) with seven collagenous amino acids (zig-zags).
Figure 3A:
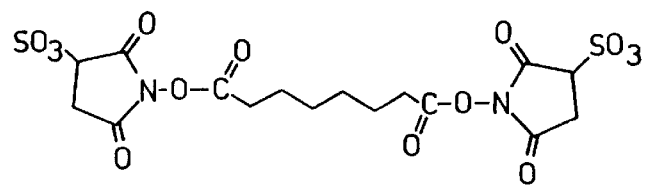
FIG. 3(a) shows the crosslinking agent, bis-(sulphosuccinimidyl) -suberate, used to react with amino-groups present within the neck-region peptide at 7 residues (Lysines), to form amide bonds, thus covalently linking polypeptide chains, spaced by 6 CH2 groups.

Using size exclusion chromatography, under non-dissociating conditions, the 65- residue-long peptide run as a single peak having an apparent molecular weight of 21–24 kDa. SDS-PAGE analysis showed single chain size of 6 kDa, however upon reaction with a cross-linking reagent, a single protein species of 21 kDa was detected when the reaction went to completion, while protein bands corresponding to 6, 13, and 21 kDa were seen in partially cross-linked reactions (FIGS. 3 and 4). Higher oligomers were never seen. Thus, the region expressed is sufficient to form a trimer.

In order to determine if the 7 Gly-Xaa-Yaa triplets at the N-terminal third of the peptide made any contribution to the formation of the trimer, collagenase digestion was carried out, and the molecular weight of the resulting peptide was reduced to 4 kDa. It was shown, by N-terminal sequencing, that all the collagen triplets had been removed. This did not, however, reduce the ability of the remaining peptide to form stable trimers in solution (FIG. 4).

Both peptides were also found to re-assemble into trimeric complexes even after heat-denaturation (98° C. for 20 min in phosphate buffered saline) and mixing varying portions of collagenase digested and intact neck-peptide followed by heat-denaturation and cooling resulted in heterotrimerization to complexes in the expected stochiometric amounts (FIGS. 5 and 6). Therefore, the C-terminal 35 residues were sufficient to mediate the stable non-covalent reversible association into trimeric complexes.

In order to obtain a complete structure determination of the neck-region peptide heteronuclear single quantum coherence ($^1$H, $^{15}$N) NMR spectra on $^{15}$N labelled peptide were collected and showed only one magnetic environment for each residue. As the peptide exists as a trimer and as each residue within any one of the three α-helices shows the same magnetic environment as the corresponding residues in the other chains the structure of the α-helical bundle must have a 3-fold symmetry. Thus, the neck-peptide assumes the same oligomeric structure as the trimeric stalk of influenza hemagglutinin [13], but, unlike the virus stalk region peptide, the SP-D peptide formed a trimeric structure over a wide range of pH (3.0–9.5). The 3-fold symmetry observed proves the non-staggered and parallel association of the three helices and is contrasted by the staggered alignment of anti-parallel helices demonstrated recently for the spectrin molecule [14]. Surprisingly, therefore, the association of three right-handed α-helices in a parallel and non-staggered left-handed superhelix can serve as the nucleation site for the formation of a right-handed collagen superhelix of left-handed helices. As the three polypeptide chains involved are identical and as the collagen helix and the α-helical bundle are positioned in a direct junction this region of the SP-D molecule should contain a sharp bending of the peptide structure.

EXAMPLE 2
Trimerization of the N-terminal Domain of Human SP-D by Fusion to the N-terminus of the Neck-region Peptide The expression plasmid for this fusion peptide was generated by removing the DNA segment coding for the collagenous region of human SP-D from 10 μg of the original cDNA containing plasmid by restriction enzyme digestion with 4 units of Nru1 in buffer Nru1 (New England Biolabs) and subsequently with 5 units of Sma1 in buffer J (Promega) at 25° C. for 4 hours, excising the 456 bp fragment. The remaining plasmid was purified using the magic miniprep DNA purification resin (Promega), re-ligated, and transformed into the competent cells of the BL21 bacterial strain of *E.coli*. The polymerase chain reaction was used to generate a BamH1 restriction enzyme site at the N-terminal end of the N-terminal domain of SP-D. The resulting PCR product was cleaved with BamH1 and Bal1 to result in an open reading frame coding for 84 amino acids (28 of the N-terminal domain and 56 of the neck-region including a 7 triplet collagenous linker between the two domains). The polypeptide was generated as a glutathione-S-transferase-N-term-neck-region fusion protein, illustrated in FIG. 7.

Individual colonies of BL21 carrying the recombinant plasmid, pGex-2T-N-term-neck, were identified to express a recombinant fusion protein of the expected (34 kDa) size after induction of protein expression with IPTG (see Example 1). Large scale protein production was performed roughly as described above for the neck-region peptide, due to a similar behaviour of the N-terminal-neck-region protein on Highload S anion exchange chromatography.

Briefly, protein expression was induced using IPTG. The cells of 6 l bacterial culture were harvested by centrifugation at 5 k rpm at 0° C. and resuspended in a buffer consisting of 100 mM Tris.Cl, pH 8.0, 200 mM NaCl, 20 mM EDTA, and the cells were lysed by sonnication for 2 minutes on ice. Cell debris was spun down at 19 k rpm for 30 minutes at 0° C. and the supernatant was applied to a glutathione-agarose affinity column, equilibrated in the lysis buffer. The resin was washed using the lysis buffer containing 0.2% (w/v) Emulphogen (polyoxyethylene-10-tridecyl ether) until the absorbance at 280 nm reached the starting value again. Bound peptides were eluted using 20 mM glutathione (reduced form) in lysis buffer and thrombin digestion was carried out in this buffer at 37° C. for 10 hours by adding 10 units of thrombin per mg of fusion peptide. The pH was then adjusted to 3.0 by adding a 1 M sodium citrate buffer, and subsequently 1 M HCl, to result in a 100 mM citrate buffered solution of pH 3.0. At this stage, a white precipitate, containing glutathione-S-transferase, was removed by centrifugation (19 k rpm at 0° C. for 30 min) and the supernatant was applied to a Pharmacia HighLoad S column for anion exchange chromatography using a Waters FPLC system. The N-terminus-neck-region peptide eluted at 450 mM NaCl in a single, symmetrical peak and was shown to be free of contaminating proteins as judged by SDS-PAGE analysis and Coomassie blue R-250 staining. The purified peptide was dialysed against PBS and concentrated using 3 kDa cut-off centricon cartridges. A 25 ml solution of the peptide in PBS of a final concentration of 1 mg/ml was recovered. This represents a yield of 4 mg/l bacterial culture of recombinant proteolytically processed peptide. The purity of the peptide as well as its size was determined by SDS-PAGE analysis to have a molecular weight of approximately 9 kDa.

Crosslinking experiments were conducted as described above for the neck-region peptide alone, and the results are shown in FIG. 8. In the absence of the covalent crosslinker the peptide behaves as a single polypeptide species of ca. 9 kDa, however, under crosslinking conditions additional bands are visible, of 18 kDa and ca. 29 kDa, corresponding to the dimeric and trimeric polypeptides in partially crosslinked complexes, and to the completely crosslinked trimeric complex present in solution. The neck-region has thus trimerized a heterologous protein domain which was fused to the N-terminus of the neck-region sequence.

EXAMPLE 3
Trimerization of the C-type Lectin Domain of Human SP-D, Positioned at the C-terminal End of the Neck-region In addition to these studies a protein expression system was employed which generates non-fusion polypeptides, thus giving a more accurate picture of the trimerizing features of the neck-region peptide.

The pET series of expression vectors (Studier and Moffat, 1986) can be used to generate high-level intracellular production of non-fusion proteins in *E.coli* using IPTG as an inducer of protein expression. In order to use the plasmid pET 3a for the production of SP-D-neck-lectin and SP-D-lectin proteins the DNA inserts coding for the SP-D derived polypeptides were excised from the pGex-2T vectors using the restriction enzymes BamH1 and EcoR1 and the resulting fragments were ligated into the chloramphenicol-resistancy carrying version of the pBluescript plasmid, pBCSK, linearized with BamH1 and RcoR1, and phosphatase-treated. The resulting plasmids, identified to contain the respective inserts using the magic miniprep method and restriction enzyme digestions, were digested with the restriction enzyme combination Xba1 and EcoRV. This generated fragments with compatible ends to the pET-3a plasmid digested with Nhe1 and EcoRV. Thus, both DNA fragments, coding for the neck-region and the lectin domain or only the lectin domain of SP-D were transfered from a fusion protein generating expression system to the pET system in a 2-step procedure. The additional residues, introduced at the N-terminal end of each of the constructs, were considered to be of minor influence, since they are unlikely to influence oligomerization of the recombinant proteins or binding to carbohydrate structures (FIG. 9). Both polypeptides were induced using IPTG and purified after lysis of the cells by conventional FPLC chromatography. Since both of the recombinant polypeptides were found to bind to FastFlow Q-Sepharose (Pharmacia) at pH 9.0 during the first step of purification, subsequent further purification was achieved on MonoQ (lectin domain) and MonoS (neck-lectin domain) columns (Pharmacia).

Figure 10:
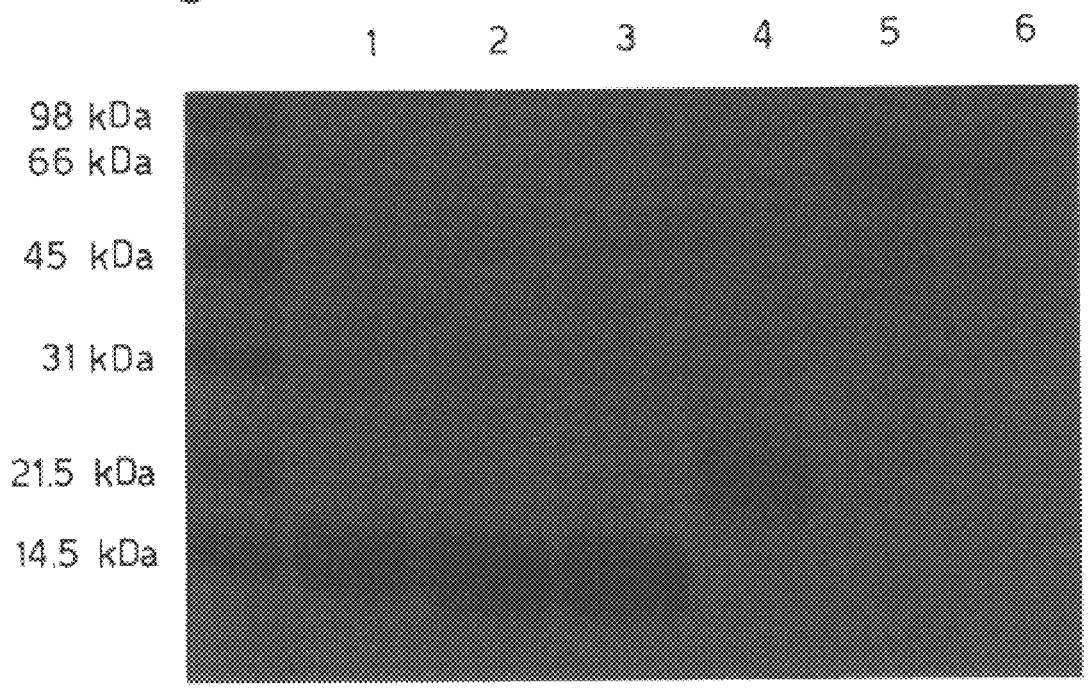

The purified proteins were dialysed against PBS at 4° C. and samples (50 μl) were analysed on 12.5% SDS-PAGE gels. Bis-(sulfosuccinimidyl)-suberate amino-reactive crosslinker was added at 2 different concentrations and the protein bands detected in lanes corresponding to these samples revealed that the two proteins differed in respect to their oligomeric status (FIG. 10). The C-type lectin domain was found to behave like a monomeric protein in solution whereas the neck-lectin domain showed the expected crosslinking pattern of a trimeric molecule in solution. Thus, the neck-region mediates the trimerization of the C-type lectin domain of human SP-D which is shown to form a monomeric molecule without the neck-region. The trimerized lectin domains were also found to bind more strongly to the affinity matrix maltose-agarose, whereas the monomeric lectin domain (without the neck-region) showed a weaker affinity (data not shown).

The two proteins expressed may provide valuable tools for the study of native carbohydrate ligands for human SP-D, since the three lectin domains in the neck-lectin molecule are expected to have the same spacing of their binding sites for carbohydrates as the lectin domains present in a single 'rod' of native human SP-D. These results indicate also that heterologous protein domains, fused to the neck-region peptide, will form trimeric complexes.

20 μg of recombinant neck-lectin polypeptide were mixed with 40 μg of neck-region peptide at 25 degree C. The mixture was analysed using a FPLC Superose 12 (Pharmacia) size exclusion chromatography column, equilibrated in PBS. The remaining solution was heated to 50 degree C for 30 min and subsequently left to cool to room temperature over a 20 min period. 100 μl of the solution were then analysed on the same Superose 12 column.

Figure 11A:
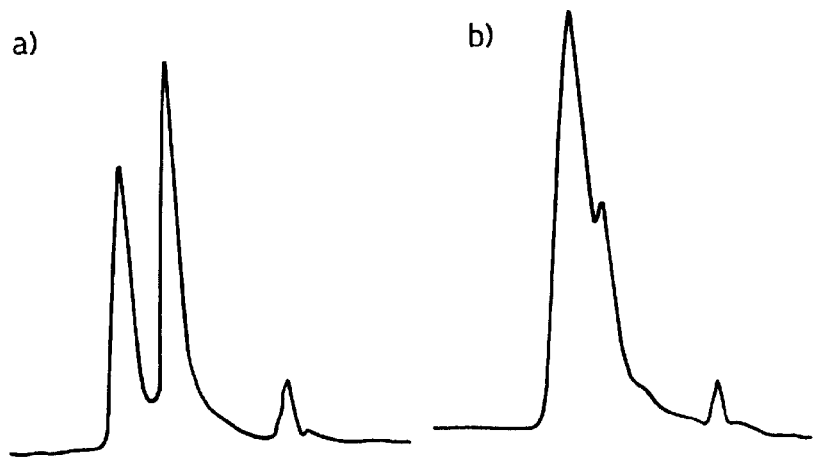
Figure 11B:
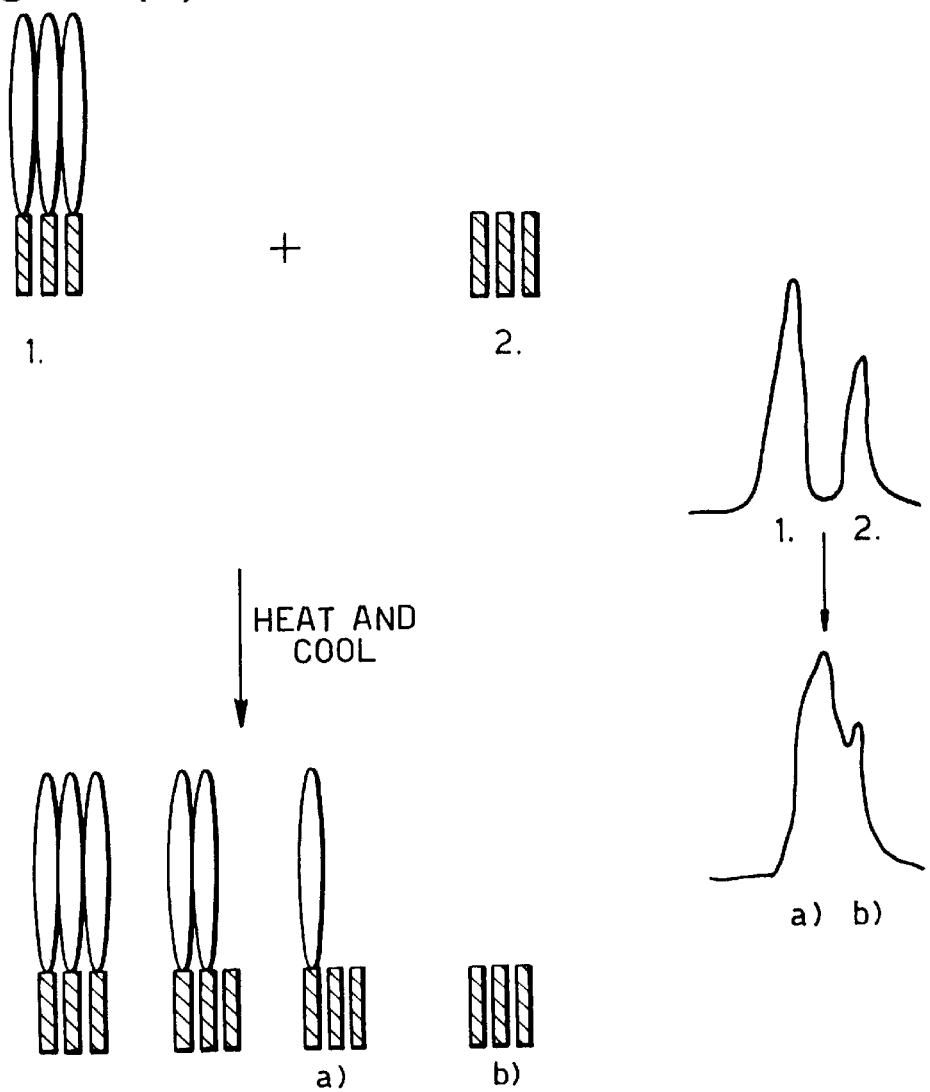

The elution profiles of both runs are illustrated in FIG. 11. Two distinct peaks corresponding to the sizes of the respective homotrimers of neck-region peptide and neck-lectin polypeptide were detected in the first run (FIG. 11 A a)), whereas the profile of the heat-treated peptide mixture had changed (FIG. 11 A b)). The first peak corresponding to the neck-lectin homotrimer shifted to a later elution time, corresponding to a smaller size. The second peak, caused by the neck-region peptide homotrimer remained at its original position, but was reduced in hight, indicating a reduced amount of neck-region peptide homotrimer. The shifted first peak was found in crosslinking experiments (data not shown) to consist of 2 neck-region peptides and 1 neck-lectin polypeptide, held together as a heterotrimeric complex.

Therefore a heterotrimerization had occurred via the neck region's-α-helices which are contained within the sequences of both polypeptides. The large molecular excess of neck-region peptide homotrimers at the beginning of the heterotrimerizing experiment has driven the reaction to yield only two trimeric complexes, namely the neck-region peptide homotrimer and a single species of heterotrimer with one neck-lectin polypeptide and two neck-region peptides. An increased concentration of the neck-lectin homotrimer at the beginning of the experiment drives the reaction to the other extreme, resulting in neck-lectin homotrimers being re-formed and a single species of heterotrimeric complexes consisting of two molecules neck-lectin polypeptide and one neck-region peptide (data not shown).

EXAMPLE 4

Nucleation of Collagen Triple-helix Formation

Figure 12A:
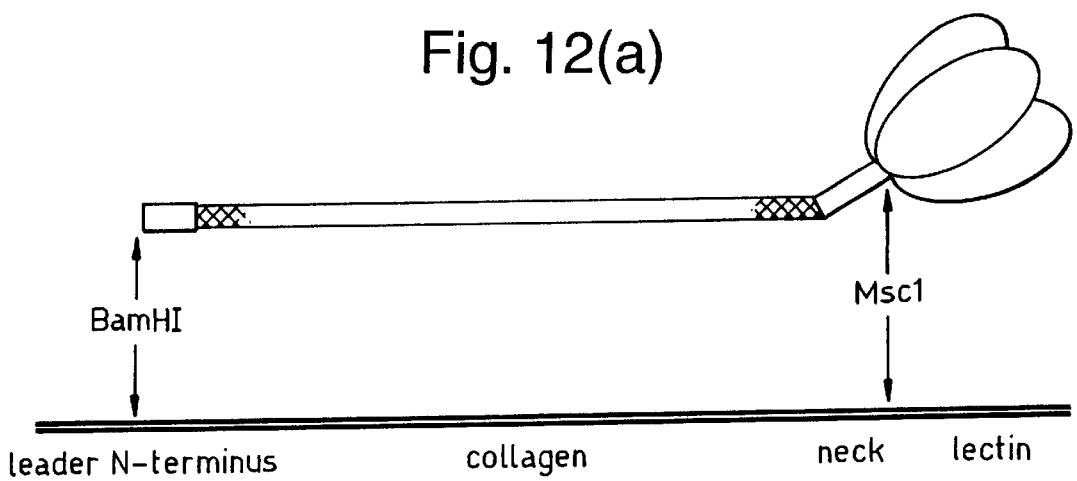
Figure 12B:
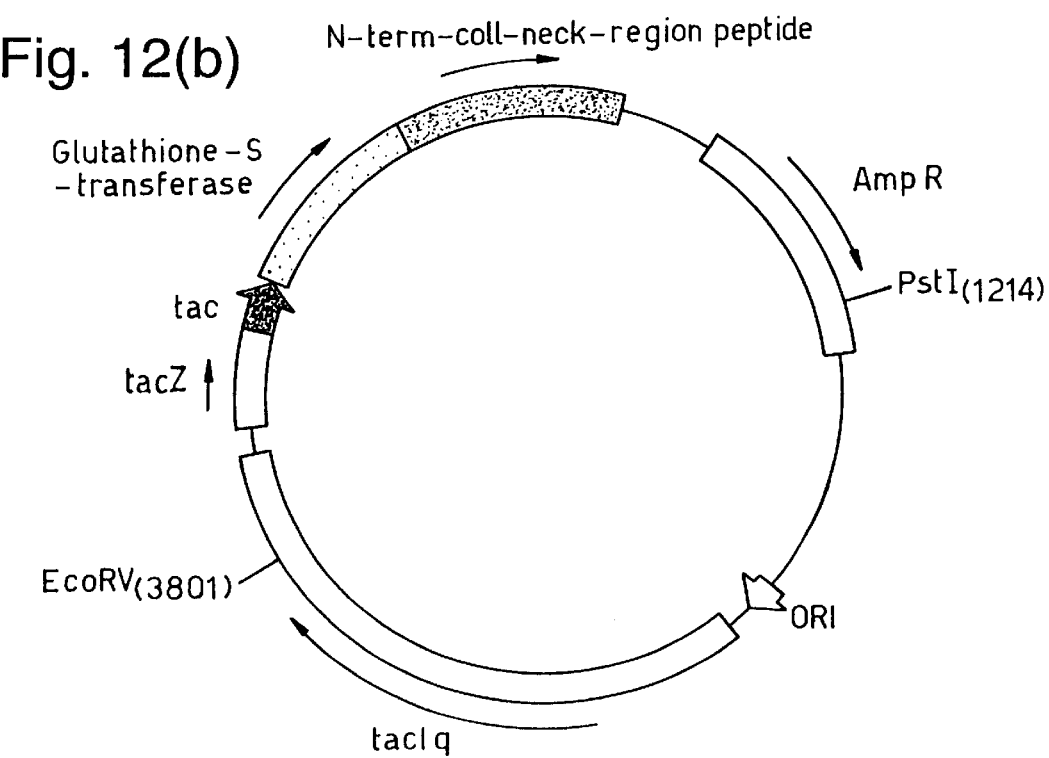

Two DNA constructs were made to generate fusion proteins with glutathione-S-transferase (see example 1): the neck-region-peptide with 57 triplets (FIG. 12) and the N-terminal non-collagenous residues of human SP-D, and 48 Gly-Xaa-Yaa triplets derived from human SP-D without the neck-region peptide fused directly to the glutathione-S-transferase. Both fusion proteins were generated and purified using the protocol outlined in Example 1.

Prior to the cleavage with thrombin the fusion proteins were diluted tenfold in 2 M glycine buffer at pH 7.5 and subsequently dialysed extensively against 100 mM Tris.HCl (pH 7.4) 200 mM NaCl. The thermal stability of polypeptides in solution may be greatly enhanced by the addition of 2 M glycine [24].

Upon digestion with thrombin and subsequent SDS-PAGE analysis marked differences were seen in the sizes of the cleavage products. The fusion protein consisting of the glutathione-S-transferase and the 48 Gly-Xaa-Yaa triplets only gave rise to a large number of peptides of different length, reflecting the frequently occurring cleavage by thrombin of peptide bonds involving arginine residues within the collagenous sequence (data not shown). In contrast, the glutathione-S-transferase fusion protein containing the neck-region peptide C-terminal to the 57 Gly-Xaa-Yaa triplets and the N-terminal non-collagenous peptide from human SP-D showed only a single cleavage into two products, the glutathione-S-transferase and the entire collagenous region with the neck-region peptide and the N-terminal peptide of human SP-D attached (FIG. 14). As the 48 Gly-Xaa-Yaa triplets of the first construct were contained in the 57 Gly-Xaa-Yaa triplets of the second construct, the absence of thrombin cleavage at any of the arginine residues is consistent with the presence of collagen triple-helical structure.

The formation of a collagen triple-helix (FIG. 13) can be detected by circular dichroism [25], multi-dimensional NMR [26], and electron microscopy [27].

The involvement of the N-terminal non-collagenous region of human SP-D in the observed increase of stability of the triple-helix can be examined. Thus, as the natural occurrence of coiled-coils at the N-terminal end of collagenous sequences is seen in the macrophage scavenger receptor, short peptide sequences are attached to N-terminal end of the collagenous regions N-terminal of the neck-region peptide using protein engineering techniques. This involves the use of polymerase chain reactions with synthesised oligonucleotides and subsequent ligations into the fusion-protein combining-site in the pGEX-2T vector, already carrying the DNA encoding the neck-region (see example 1).

The resulting set of purified recombinant peptides is tested for correct alignment of triple-helical peptides using amino-reactive chemical crosslinking-reagents in combination with SDS-PAGE and size-exclusion chromatography. A few suitable peptides are then $^{15}$N-isotope labelled and analysed for thermal stability using multi-dimensional NMR. At this stage the influence of the triplet number on the melting temperature is examined by subsequent insertion of longer stretches of collagen-coding DNA in a similar fashion.

EXAMPLE 5
Increased Binding of C-type Lectin Domain of SP-D When Trimerised Using Neck Region Peptide The pBluescript plasmid containing cDNA coding for human SP-D protein was digested with the restriction enzymes Sma1 and EcoR1, as well as with Msc1 and EcoR1, giving rise to DNA fragments of 532 bp, and 364 bp, respectively. Both fragments were subcloned into the pGex-2T expression vector, linearized with the restriction enzymes Sma1 and EcoR1. This directional cloning procedure produced two expression plasmids, pGex-2T-neck-lectin and pGex-2T-lectin, which were transformed into the E.coli BL21 strain. Protein expression was induced with IPTG and clones identified to produce recombinant proteins of the expected size, i.e. 43 kDa for pGex-2T-neck-lectin and 37 kDa for pGex-2T-lectin (FIG. 15), were used to start large-scale preparation of glutathione-S-transferase containing fusion proteins, as described above.

Following cell lysis by sonnication and removal of the cell debris by centrifugation, a portion of the supernatant (corresponding to 100 ml of the original bacterial culture) was made 5 mM in respect to unchelated calcium, and the solution was diluted ten-fold in 100 mM Tris.Cl, 150 mM NaCl, 5 mM $CaCl_2$, 1 mM $NaN_3$, pH 7.5. The resulting solution was dialysed against 10 l of the same buffer at 4° C. overnight, and after removal of some additionally formed precipitate by centrifugation the protein solution was passed, at 10 ml/hour, over a maltose-agarose column, equilibrated in the same buffer. The column was washed with 50 ml of the buffer and bound proteins were eluted using 20 mM EDTA in 100 mM Tris.Cl, 150 mM NaCl, pH 7.5.

Samples (50 μl) were analysed on 12.5% SDS-PAGE gels, but only the pGex-2T-neck-lectin encoded protein of approximately 43 kDa could be purified in this way. Apparently, the fusion protein containing only the C-type lectin domain fused to the glutathione-S-transferase was not able to bind to the immobilized maltose under the conditions used (FIG. 16). This observation is consistent with the suspected role of the neck-region peptide in bringing together three identical polypeptide chains, in a parallel orientation, and thus enhancing the binding properties of the adjacent C-type lectin domains.

EXAMPLE 6
Trimerization of a Single-chain Antibody

Total RNA prepared from the hybridoma cell line OX35 [15] was used as a template for cDNA-PCR [16] to generate DNA encoding the variable region of the light and heavy chain of the anti-CD4 monoclonal antibody secreted by the hybridoma cells. Both fragments, of 400 bp length, were cloned into the pBluescript SK vector (Stratagene) and subsequently combined using a synthetic DNA fragment encoding the semi-rigid linker-peptide $(GGGGS)_3$ (SEQ ID NO:13), which ensured the correct pairing of the $V_L$ and $H_L$ domains [17]. The sequence of the construct was confirmed by dideoxy sequencing of the DNA.

The DNA fragment encoding for the two variable IgG domains, linked by the GGGGS-linker (SEQ ID NO:13), was then cloned into the pGEX-2T vector, already carrying the neck-region peptide gene (see example 1), to give rise to a fusion protein, GT-OX35-scAb-neck, (of an expected molecular weight of 55 kDa) consisting of the single-chain antibody, as well as the glutathione-S-transferase and the neck-region peptide. The single-chain antibody encoding DNA was also cloned into the pGEX-2T vector alone, without the neck-region peptide gene, giving rise to an open reading frame coding for the OX35-scAb fused to the glutathione-S-transferase (resulting in a fusion protein of 50 kDa). Both expression vectors constructed were transformed into E.coli BL21 cells (see FIG. 17).

Expression levels were found to be similar to that obtained with the neck-region peptide alone (Example 1) (see FIG. 18). However, following the purification protocol, as outlined in example 1, most of the fusion protein was found to be insoluble and only a small proportion of the single-chain antibody fusion proteins could be solubilized and purified using a glutathione-agarose affinity column. Upon cleavage with thrombin fragments of the expected size were detected using SDS-PAGE analysis. Minor amounts of smaller fragments were also seen.

The single chain antibody containing polypeptides were purified and on SDS-PAGE analysis had an apparent molecular weight of 25 kDa for the OX35-scAb and 30 kDa for the OX35-scAb-neck polypeptides, however, using size-exclusion chromatography, an increased apparent molecular weight was observed for OX35-scAb-neck, whereas the OX35-scAb showed the expected behaviour of a 25 kDa polypeptide on the size exclusion column.

Chemical cross-linking experiments, as well as sucrose density centrifugation analysis, determine the oligomeric status of the OX35-scAb-neck polypeptide. Estimation based only on the results obtained in the gel filtration analysis provide indication of the presence of a trimeric molecule. Affinity measurements with the trimeric and monomeric scAbs using immobilized recombinant CD4 [18] in ELISA and BiaCore Plasmon Resonance [19] analysis may be carried out. A substantial improvement of yield and structural uniformity of the expressed antibody constructs may be obtained by following established protocols for the purification of recombinant proteins from bacterial inclusion bodies [20] or the use of a yeast expression system, known to facilitate expression of disulphide containing molecules [21].

References

1. Traub, W. and Piez, K. A. (1971) *Adv. Protein Chem.* 25, 243–352.
2. Labourdette, L., Rest, M.v.d. (1993) *FEBS Lett.* 320, 211–214.
3. Engel, J., Prockop, D. J. (1991) *Annu.Rev.Biocphys.Biophys.Chem.* 20, 137–152.
4. Bork, P. (1992) *FEBS Lett.* 307, 49–54.
5. Holmskov, U., Malhotra, R., Sim., R. B., Jensenius, J. C. (1994) *Immunol. Today* 15, 67–73.
6. Weis, W. I., Kahn, R., Fourme, R., Drickamer, K., Hendrickson, W. A, (1988) *Science* 254, 1608–1615.
7. Hoppe, H.-J., Barlow, P. N., Reid, K. B. M. A three stranded α-helical bundle at the nucleation site of collagen triple-helix formation in human surfactant protein D (1994) *FEBS Letters* 344, 191–195.
8. Norwood, T. J., Boyd, J., Heritage, J. E., Soffe, N., Campbell, I. D. (1990) *J. Magn. Reson.* 87, 9638–9644.
9. Smith, D. B., Johnson, K. S. (1988) *Gene* 67, 31–40.
10. Chen, Y.-H., Yang, J. T., Chau, K. H. (1974) *Biochemistry* 13, 3350–3359.
11. Pauling, L., Corey, R. B. (1953) *Nature* 171, 59–61.
12. Harbury, P. B., Zhang, T., Kim, P. S., Alber, T. (1993) *Science* 262, 1401–1407.
13. Carr, C. M., Kim, P. S. (1993) *Cell* 73, 823–832.
14. Yan, Y., Winograd, E., Viel, A., Cronin, T., Harrison, S. C., Branton, D. (1994) *Science* 262, 2027–2030.
15. Ilano, A L, McConnell, M V, Gurley, K E, Spinelli, A, Pearce, N W, Hall, B M Cellular basis of allograft rejection in vivo. V. Examination of the mechanisms responsible for the differing efficacy of monoclonal antibody to CD4+ T cell subsets in low- and high responder rat strains (1989) *Journal of Immunology* 143, 2828–2836

16. Chaudhary, V. K., Batra, J. K., Gallo, M. G., et al A rapid method of cloning functional variable-region antibody genes in *Escherichia coli* as single-chain immunotoxins (1990) *Proc.Natl.Acad.Sci USA* 87, 1066–1070
17. Pluckthun, A. Mono- and bivalent antibody fragments produced in *E.coli:* engineering, folding and antigen binding. (1992) *Immunol.Rev.* 130, 209–216.
18. Ashford, D A, Alafi, C D, Gamble, V M, Mackay, D J G, Rademacher, T W, Williams, P J, Dwek, R A, Barclay, A N, Davis, S J, Somoza, C, Ward, H A, Williams, A F (1993) Site-specific glycosylation of recombinant rat and human soluble CD4 variants expressed in Chinese hamster ovary cells *Journal of Biological Chemistry* 268, 3260–3267.
19. Malmqvist, M Surface plasmon resonance for detection and measurement of antibody-antigen affinity and kinetics 1993 *Current Opinion in Immunology* 5, 282–286.
20. Murray P. Deutscher (edt.), Guide to Protein Purification (1990) *Methods in Enzymology,* Volume 182 , Academic Press, INC.
21. Kaslow, D C, Hui, G, Kumar, S Expression and antigenicity of Plasmodium falciparum major merozoite surface protein (MSP119) variants secreted from *Saccharomyces cerevisiae* (1994) *Molecular and Biochemical Parasitology* 63, 283–289.
22. Bachinger, H P, Morris, N P, Davis, J M Thermal stability and folding of the collagen triple helix and the effects of mutations in osteogenesis imperfecta on the triple helix of type I collagen (1993) *American Journal of Medical Genetics* 45, 152–162.
23. Fan, P, Li, M H, Brodsky, B, Baum, J Backbone dynamics of (Pro-Hyp-Gly)10 and a designed collagen-like triple-helical peptide by 15N NMR relaxation and hydrogen-exchange measurements (1993) *Biochemistry (USA)* 32, 13299–13309.
24. Matthews, S. J., Leatherbarrow, R. J. The use of osmolytes to facilitate protein NMR spectroscopy (1993) *J. Biomolecular NMR* 3, 597–600.
25. Haas, C, Voss, T, Engel, J Assembly and disulfide rearrangement of recombinant surfactant protein A in vitro (1991) *European Journal of Biochemistry* 197, 799–803.
26. Long, C G, Braswell, E, Zhu, D, Apigo, J, Baum, J, Brodsky, B Characterization of collagen-like peptides containing interruptions in the repeating Gly-X-Y sequence (1993) *Biochemistry (USA)* 32, 11688–11695.
27. Lu, J, Wiedemann, H, Holmskov, U, Thiel, S, Timpl, R, Reid, KBM Structural similarity between lung surfactant protein D and conglutinin. Two distinct, C-type lectins containing collagen-like sequences (1993) *European Journal of Biochemistry* 215, 793–799.

What is claimed is:

1. A non-naturally occurring polypeptide which comprises a first sequence of amino acids which is a neck-region of a collectin, fused to one or more heterologous amino acids, and which forms a trimer.

2. A polypeptide according to claim 1 wherein the first sequence of amino acids is the neck-region of collection Lung Surfactant Protein D (SP-D).

3. A polypeptide according to claim 1 wherein the first amino acid sequence is the neck-region amino acid sequence shown in SEQ ID NO:7.

4. A polypeptide according to claim 3 wherein the heterologous amino acids comprise an immunoglobulin sequence.

5. A polypeptide according to claim 3 wherein the first amino acid sequence is joined to heterologous amino acid or acids via a peptide linker.

6. A polypeptide according to claim 3 wherein the heterologous amino acid is or heterologous amino acids comprise an amino acid which is derivatizable for attachment of a chemical moiety.

7. A polypeptide according to claim 3 wherein the heterologous amino acids comprise a protein domain.

8. A polypeptide according to claim 3 joined to a non-peptide moiety.

9. A nucleic acid comprising a sequence of nucleotides encoding a polypeptide according to claim 3.

10. A nucleic acid according to claim 9 wherein said nucleic acid further comprises a vector.

11. A host cell containing the nucleic acid according to claim 9.

12. A nucleic acid according to claim 9 wherein the encoding sequence is operably linked to a regulatory sequence for expression of the polypeptide.

13. A host cell containing the nucleic acid according to claim 12.

14. A trimer comprising the polypeptide according to claim 3.

15. A trimer according to claim 14 which is a homotrimer.

16. A trimer according to claim 14 which is a heterotrimer.

17. A polypeptide according to claim 1 wherein the first amino acid sequence is the neck region of collectin-43 or conglutinin.

18. A non-naturally occurring polypeptide that forms a trimer and that comprises a first sequence of amino acids that is a neck-region of a collectin that contains at least one substitution of an amino acid residue, wherein said substitution is determined by amino acid sequence alignment of said neck-region with a neck-region of a different collectin to be present at the corresponding position in said neck-region of said different collectin, wherein said substitution does not abolish trimerization, fused to one or more heterologous amino acids.

19. A polypeptide according to claim 1 or 18 wherein the heterologous amino acids comprise a protein domain.

20. A polypeptide according to claim 1 or claim 18 wherein the heterologous amino acids comprise an immunoglobulin sequence.

21. A polypeptide according to claim 1 or claim 18 wherein the first amino acid sequence is joined to heterologous amino acid or acids via a peptide linker.

22. A polypeptide according to claim 1 or claim 18 wherein the heterologous amino acid is or heterologous amino acids comprise an amino acid which is derivatisable for attachment of a chemical moiety.

23. A polypeptide according to claim 1 or claim 18 joined to a non-peptide moiety.

24. A polypeptide according to claim 1 or claim 18 comprising said heterologous amino acid(s) N-terminal to the first sequence of amino acids and one or more amino acids C-terminal to the first sequence of amino acids, or said heterologous amino acid(s) C-terminal to the first sequence of amino acids and one or more amino acids N-terminal to the first sequence of amino acids.

25. A polypeptide according to claim 1 or claim 18 comprising a collectin C-type lectin domain.

26. Nucleic acid comprising a sequence of nucleotides encoding a polypeptide according to claim 1 or claim 18.

27. Nucleic acid according to claim 26 which is a vector.

28. A host cell containing nucleic acid according to claim 26.

29. Nucleic acid according to claim 26 wherein the encoding sequence is operably linked to a regulatory sequence for expression of the polypeptide.

30. A host cell containing nucleic acid according to claim 29.

31. A method comprising culturing a host cell according to claim 30 under conditions for expression of said polypeptide.

32. A method comprising expression from nucleic acid according to claim 26 of the encoded polypeptide.

33. A method comprising forming a trimer comprising a polypeptide following its expression according to the method of claim 32.

34. A method according to claim 33 wherein said trimer is a homotrimer.

35. A method according to claim 33 wherein said trimer is a heterotrimer.

36. A method comprising forming a trimer comprising a polypeptide according to claim 1 or claim 18.

37. A trimer comprising a polypeptide according to claim 1 or claim 18.

38. A trimer according to claim 37 which is a homotrimer.

39. A trimer according to claim 37 which is a heterotrimer.

40. A method of forming a collagenous triple helix comprising providing non-naturally occurring polypeptides, each polypeptide comprising a series of collagenous triplets N-terminal to a first sequence of amino acids which is a neck-region of a collectin and bringing into contact said polypeptides to form trimers.

41. A method according to claim 40 wherein the first sequence of amino acids is the neck-region of collectin Lung Surfactant Protein D (SP-D).

42. A method according to claim 40 wherein the first amino acid sequence is the neck-region amino acid sequence shown in SEQ ID NO:7.

43. A method according to claim 40 wherein the first amino acid sequence is the neck region of collectin-43 or conglutinin.

44. A method according to claim 40 wherein said first sequence of amino acids is at the C-terminus of the polypeptide.

45. A method according to claim 40 wherein said non-naturally occurring polypeptide comprises one or more heterologous amino acids C-terminal to said first sequence.

46. A method of forming a collagenous triple helix comprising providing non-naturally occurring polypeptides, each polypeptide comprising a series of collagenous triplets N-terminal to a first sequence of amino acids that is a neck-region of a collectin that contains at least one substitution of an amino acid residue, wherein said substitution is determined by amino acid sequence alignment of said neck-region with a neck-region of a different collectin to be present at the corresponding position in said neck-region of said different collectin, wherein said substitution does not abolish trimerization, and bringing into contact said polypeptides to form trimers.

47. A method according to claim 40 or claim 46 wherein said polypeptides are provided by expression from encoding nucleic acid therefor.

48. A method according to claim 47 wherein said trimers are isolated following trimerisation.

49. A polypeptide consisting of a neck-region of a collectin, wherein said polypeptide forms a trimer.

50. A polypeptide according to claim 49 wherein said polypeptide is chemically attached to a heterologous polypeptide.

51. A trimer of three polypeptides according to claim 49.

52. A trimer according to claim 51 wherein one of said polypeptides in said trimer is chemically attached to a heterologous polypeptide.

53. A nucleic acid encoding the polypeptide according to claim 49.

54. A polypeptide consisting of the neck-region amino acid sequence shown in SEQ ID NO:1, wherein said polypeptide forms a trimer.

55. A polypeptide according to claim 54 wherein said polypeptide is chemically attached to a heterologous polypeptide.

56. A trimer of three polypeptides according to claim 54.

57. A trimer according to claim 56 wherein one of said polypeptides in said trimer is chemically attached to a heterologous polypeptide.

58. A nucleic acid encoding the polypeptide according to claim 54.

59. A polypeptide consisting of a sequence of amino acids that is a neck-region of a collectin that contains at least one substitution of an amino acid residue, wherein said substitution is determined by amino acid sequence alignment of said neck-region with a neck-region of a different collectin to be present at the corresponding position in said neck-region of said different collectin, wherein said substitution does not abolish trimerization, wherein said polypeptide forms a trimer.

60. A polypeptide according to claim 59 wherein said polypeptide is chemically attached to a heterologous polypeptide.

61. A trimer of three polypeptides according to claim 59.

62. A trimer according to claim 61 wherein one of said polypeptides in said trimer is chemically attached to a heterologous polypeptide.

63. A nucleic acid encoding the polypeptide according to claim 59.

* * * * *

UNITED STATES PATENT AND TRADEMARK OFFICE
CERTIFICATE OF CORRECTION

PATENT NO.      : 6,190,886 B1                                            Page 1 of 1
DATED           : February 20, 2001
INVENTOR(S)     : Hoppe et al.

It is certified that error appears in the above-identified patent and that said Letters Patent is hereby corrected as shown below:

Drawings,
Sheet 1 of 16, replace:

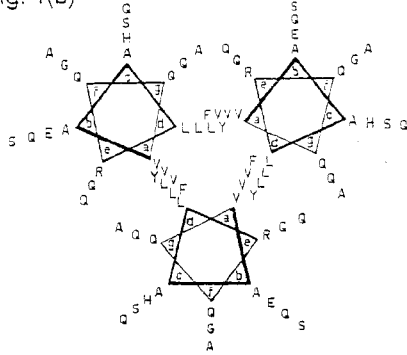

with: Fig. 1(b)

Signed and Sealed this

Second Day of December, 2003

JAMES E. ROGAN
*Director of the United States Patent and Trademark Office*

```
                       SEQUENCE LISTING (1) GENERAL INFORMATION:

(iii) NUMBER OF SEQUENCES: 13

(2) INFORMATION FOR SEQ ID NO: 1:

(i) SEQUENCE CHARACTERISTICS:
          (A) LENGTH: 27 amino acids
          (B) TYPE: amino acid
          (D) TOPOLOGY: linear (ii) MOLECULE TYPE: peptide (xi) SEQUENCE DESCRIPTION: SEQ ID NO: 1:

Val Ala Ser Leu Arg Gln Gln Val Glu Ala Leu Gln Gly Gln Val Gln
1               5                   10                  15

His Leu Gln Ala Ala Phe Ser Gln Tyr Lys Lys
            20                  25

(2) INFORMATION FOR SEQ ID NO: 2:

(i) SEQUENCE CHARACTERISTICS:
          (A) LENGTH: 27 amino acids
          (B) TYPE: amino acid
          (D) TOPOLOGY: linear (ii) MOLECULE TYPE: peptide (xi) SEQUENCE DESCRIPTION: SEQ ID NO: 2:

Val Asn Ala Leu Arg Gln Arg Val Gly Ile Leu Glu Gly Gln Leu Gln
1               5                   10                  15

Arg Leu Gln Asn Ala Phe Ser Gln Tyr Lys Lys
            20                  25

(2) INFORMATION FOR SEQ ID NO: 3:

(i) SEQUENCE CHARACTERISTICS:
```

(A) LENGTH: 27 amino acids
       (B) TYPE: amino acid
       (D) TOPOLOGY: linear (ii) MOLECULE TYPE: peptide (xi) SEQUENCE DESCRIPTION: SEQ ID NO: 3:

Ser Ala Ala Leu Arg Gln Gln Met Glu Ala Leu Asn Gly Lys Leu Gln
1               5                   10                  15

Arg Leu Glu Ala Ala Phe Ser Arg Tyr Lys Lys
            20                  25

(2) INFORMATION FOR SEQ ID NO: 4:

(i) SEQUENCE CHARACTERISTICS:
       (A) LENGTH: 27 amino acids
       (B) TYPE: amino acid
       (D) TOPOLOGY: linear (ii) MOLECULE TYPE: peptide (xi) SEQUENCE DESCRIPTION: SEQ ID NO: 4:

Val Asn Ala Leu Lys Gln Arg Val Thr Ile Leu Asp Gly His Leu Arg
1               5                   10                  15

Arg Phe Gln Asn Ala Phe Ser Gln Tyr Lys Lys
            20                  25

(2) INFORMATION FOR SEQ ID NO: 5:

(i) SEQUENCE CHARACTERISTICS:
       (A) LENGTH: 27 amino acids
       (B) TYPE: amino acid
       (D) TOPOLOGY: linear (ii) MOLECULE TYPE: peptide (xi) SEQUENCE DESCRIPTION: SEQ ID NO: 5:

Val Asp Thr Leu Arg Gln Arg Met Arg Asn Leu Glu Gly Glu Val Gln
1               5                   10                  15

Arg Leu Gln Asn Ile Val Thr Gln Tyr Arg Lys
            20                  25

(2) INFORMATION FOR SEQ ID NO: 6:

(i) SEQUENCE CHARACTERISTICS:
       (A) LENGTH: 41 amino acids
       (B) TYPE: amino acid
       (D) TOPOLOGY: linear (ii) MOLECULE TYPE: peptide (xi) SEQUENCE DESCRIPTION: SEQ ID NO: 6:

Val Ala Ser Leu Arg Gln Gln Val Glu Ala Leu Gln Gly Gln Val Ala
1               5                   10                  15

Ser Leu Arg Gln Gln Val Glu Ala Leu Gln Gly Gln Val Gln His Leu
            20                  25                  30

Gln Ala Ala Phe Ser Gln Tyr Lys Lys
        35                  40

(2) INFORMATION FOR SEQ ID NO: 7:

(i) SEQUENCE CHARACTERISTICS:
       (A) LENGTH: 64 amino acids
       (B) TYPE: amino acid
       (D) TOPOLOGY: linear (ii) MOLECULE TYPE: peptide (xi) SEQUENCE DESCRIPTION: SEQ ID NO: 7:

```
Gly Ser Pro Gly Leu Lys Gly Asp Lys Gly Ile Pro Gly Asp Lys Gly
 1               5                  10                  15

Ala Lys Gly Glu Ser Gly Leu Pro Asp Val Ala Ser Leu Arg Gln Gln
                20                  25                  30

Val Glu Ala Leu Gln Gly Gln Val Gln His Leu Gln Ala Ala Phe Ser
            35                  40                  45

Gln Tyr Lys Lys Val Glu Leu Phe Pro Gly Gly Ile Pro His Arg Asp
    50                  55                  60
```

(2) INFORMATION FOR SEQ ID NO: 8:

(i) SEQUENCE CHARACTERISTICS:
        (A) LENGTH: 25 amino acids
        (B) TYPE: amino acid
        (D) TOPOLOGY: linear (ii) MOLECULE TYPE: peptide (xi) SEQUENCE DESCRIPTION: SEQ ID NO: 8:

```
Val Ala Ser Leu Arg Gln Gln Val Glu Ala Leu Gln Gly Gln Val Gln
 1               5                  10                  15

His Leu Gln Ala Ala Phe Ser Gln Tyr
                20                  25
```

(2) INFORMATION FOR SEQ ID NO: 9:

(i) SEQUENCE CHARACTERISTICS:
        (A) LENGTH: 30 amino acids
        (B) TYPE: amino acid
        (D) TOPOLOGY: linear (ii) MOLECULE TYPE: peptide (xi) SEQUENCE DESCRIPTION: SEQ ID NO: 9:

```
Gly Ser Ala Glu Met Lys Thr Tyr Ser His Arg Thr Pro Ser Ala Cys
 1               5                  10                  15

Thr Leu Val Met Cys Ser Ser Glu Ser Gly Leu Pro Gly Arg
                20                  25                  30
```

(2) INFORMATION FOR SEQ ID NO: 10:

(i) SEQUENCE CHARACTERISTICS:
        (A) LENGTH: 62 amino acids
        (B) TYPE: amino acid
        (D) TOPOLOGY: linear (ii) MOLECULE TYPE: peptide (xi) SEQUENCE DESCRIPTION: SEQ ID NO: 10:

```
Gly Leu Lys Gly Asp Lys Gly Ile Pro Gly Asp Lys Gly Ala Lys Gly
 1               5                  10                  15

Glu Ser Gly Leu Pro Asp Val Ala Ser Leu Arg Gln Gln Val Glu Ala
                20                  25                  30

Leu Gln Gly Gln Val Gln His Leu Gln Ala Ala Phe Ser Gln Tyr Lys
            35                  40                  45

Lys Val Glu Leu Phe Pro Asn Gly Gly Ile Pro His Arg Asp
    50                  55                  60
```

-continued (2) INFORMATION FOR SEQ ID NO: 11:

(i) SEQUENCE CHARACTERISTICS:
        (A) LENGTH: 7 amino acids
        (B) TYPE: amino acid
        (D) TOPOLOGY: linear (ii) MOLECULE TYPE: peptide (xi) SEQUENCE DESCRIPTION: SEQ ID NO: 11:

```
Met Ala Arg Thr Ser Gly Ser
1               5
```

(2) INFORMATION FOR SEQ ID NO: 12:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO: 12:

```
Gly Ile Pro His Arg Asp
1               5
```

(2) INFORMATION FOR SEQ ID NO: 13:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO: 13:

```
Gly Gly Gly Gly Ser Gly Gly Gly Gly Ser Gly Gly Gly Gly Ser
1               5                  10                  15
```